US009284356B2

(12) United States Patent
Chang et al.

(10) Patent No.: US 9,284,356 B2
(45) Date of Patent: Mar. 15, 2016

(54) IDENTIFICATION OF A WEST NILE VIRUS CD4 T CELL EPITOPE AND USE THEREOF

(75) Inventors: Gwong-Jen J. Chang, Fort Collins, CO (US); Holly R. Hughes, Tampa, FL (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 157 days.

(21) Appl. No.: 14/130,839

(22) PCT Filed: Jul. 11, 2012

(86) PCT No.: PCT/US2012/046269
§ 371 (c)(1),
(2), (4) Date: Jan. 3, 2014

(87) PCT Pub. No.: WO2013/009884
PCT Pub. Date: Jan. 17, 2013

(65) Prior Publication Data
US 2014/0154283 A1    Jun. 5, 2014

Related U.S. Application Data

(60) Provisional application No. 61/506,934, filed on Jul. 12, 2011.

(51) Int. Cl.
*C07K 14/005* (2006.01)
*A61K 39/00* (2006.01)
(52) U.S. Cl.
CPC ............ *C07K 14/005* (2013.01); *A61K 2039/70* (2013.01); *C12N 2770/24122* (2013.01)

(58) Field of Classification Search
None
See application file for complete search history.

(56) References Cited

U.S. PATENT DOCUMENTS

| 2005/0048073 | A1 | 3/2005 | De Groot et al. |
| 2006/0159704 | A1 | 7/2006 | Bonaldo et al. |
| 2010/0184832 | A1 | 7/2010 | Pugachev et al. |
| 2010/0255028 | A1 | 10/2010 | Delagrave et al. |
| 2011/0059131 | A1 | 3/2011 | Chang et al. |

FOREIGN PATENT DOCUMENTS

| WO | WO 01/53467 | 7/2001 |
| WO | WO 03/102166 | 12/2003 |
| WO | WO 2004/009764 | 1/2004 |
| WO | WO 2009/114207 | 9/2009 |
| WO | WO 2013/059493 | 4/2013 |

OTHER PUBLICATIONS

Crill et al., "A Detailed Mutagenesis Study of Flavivirus Cross-Reactive Epitopes using West Nile Virus-Like Particles," *J. Gen. Virol.*, vol. 88:1169-1174, 2007.

(Continued)

*Primary Examiner* — Michelle S Horning
(74) *Attorney, Agent, or Firm* — Klarquist Sparkman, LLP

(57) ABSTRACT

Described herein is the identification and of a potent West Nile virus (WNV) CD4 positive T cell epitope and its use for increasing the immunogenicity of heterologous flavivirus vaccines, such as dengue virus type 2 (DENV-2) DNA and virus-like particle (VLP) vaccines. Also described are methods for the identification of potent T cell epitopes to enhance immunogenicity of multivalent vaccines.

14 Claims, 11 Drawing Sheets

(56) References Cited

OTHER PUBLICATIONS

Crill et al., "Humoral Immune Responses of Dengue Fever Patients Using Epitope-Specific Serotype-2 Virus-Like Particle Antigens," *PLoS ONE*, vol. 4:e4991, 2009.

Crill et al., "Sculpting Humoral Immunity through Dengue Vaccination to Enhance Protective Immunity," *Front. Immunol.*, vol. 3:1-19, 2012.

Hughes, Holly Ruth, "Increasing Dengue Virus Vaccine Safety and Immunogenicity by Manipulating Antigenic Determinants of the Flavivirus Envelope Protein," Dissertation, Department of Microbiology, Immunology and Pathology, Colorado State University, Feb. 28, 2011; 217 pages. E-mail correspondence (1 page) appended to Dissertation.

Hughes et al., "Manipulation of Immunodominant Dengue Virus E Protein Epitopes Reduces Potential Antibody-Dependent Enhancement," *Virol. J.*, vol. 9:115-127, 2012.

Hughes et al., "A West Nile Virus CD4 T Cell Epitope Improves the Immunogenicity of Dengue Virus Serotype 2 Vaccines," *Virol.*, vol. 424:129-137, 2012.

Partial Supplementary European Search Report for European Application No. 12810873.5, dated Jul. 10, 2015; 7 pages.

Brinton et al., "Immune Mediated and Inherited Defenses Against Flaviviruses," *Clin. Diag. Virol.*, vol. 10:129-139, 1998.

De Groot, et al., "Rapid Determination of HLA B*07 Ligands from the West Nile Virus NY99 Genome," *Emerg. Infect. Dis.*, vol. 7:706-713, 2001.

Larsen et al., "Identification of CD8[+] T Cell Epitopes in the West Nile Virus Polyprotein by Reverse-Immunology Using NetCTL," *PLoS One*, vol. 5:e12697, 2010.

FIG. 4

IDENTIFICATION OF A WEST NILE VIRUS CD4 T CELL EPITOPE AND USE THEREOF

CROSS REFERENCE TO RELATED APPLICATIONS

This is the U.S. National Stage of international Application No. PCT/US2012/046269, filed Jul. 11, 2012, published in English under PCT Article 21(2), which claims the benefit of U.S. Provisional Application No. 61/506,934, filed Jul. 12, 2011, which is herein incorporated by reference in its entirety.

FIELD

This disclosure concerns the identification of T cell epitopes (for instance, CD4 T cell epitopes in West Nile virus) and their use for enhancing immunogenicity of vaccines, such as heterologous flavivirus vaccines, such as dengue virus vaccines.

BACKGROUND

Dengue virus (DENV), which exists as four closely related serotypes, is a single-stranded RNA virus in the flavivirus genus. With the global resurgence of DENV infections, including the DENV-1 outbreak in Key West, Fla. (CDC, MMWR 59, 577-581, 2010), dengue has evolved into one of the world's most important arboviral diseases. DENV infection causes either mild dengue fever, or severe life-threatening dengue hemorrhagic fever and dengue shock syndrome (DHF/DSS). Severe dengue is a common occurrence in children residing in hyperendemic countries and is strongly associated with secondary heterotypic infections (Sangkawibha et al., *Am J Epidemiol* 120(5): 653-669, 1984). Currently, vector control and education programs are all that are available for dengue disease prevention; and the development of dengue vaccination has been hindered by concerns of waning or imbalanced tetravalent immunity leading to vaccine induced DHF/DSS. However, a handful of vaccines are in the early stages of clinical trials (Durbin and Whitehead, *Curr Top Microbiol Immunol* 338: 129-143, 2010).

DNA vaccination has become a fast growing field in vaccine technology since the 1990s following the first reports of plasmid DNA inducing an immune response to plasmid-encoded antigen (Tang et al., *Nature* 356(6365): 152-154, 1992). Although DNA vaccines are considered by some to be one of the most important discoveries in the field of vaccinology (Mor, *Biochem Pharmacol* 55(8): 1151-1153, 1998), DNA vaccination in most cases is hampered by low immunogenicity and efficacy. Thus various strategies to improve the immune response following DNA vaccination have been developed. Earliest attempts to increase DNA vaccine immunogenicity have included optimization of route, dosage, and timing of administration; DNA encoded or exogenously administered costimulatory molecules and cytokines; and prime-boost regimens (Leitner et al., *Vaccine* 18(9-10): 765-777, 1999).

SUMMARY

Disclosed herein is the identification of a potent CD4 positive T cell epitope in the transmembrane domain (TMD) of the E-glycoprotein of West Nile virus (WNV). The identified CD4 T cell epitope can be introduced into the E-glycoprotein of other flaviviruses to enhance the immunogenicity of flavivirus vaccines.

Provided herein are isolated mutant flavivirus E-glycoprotein polypeptides that contain the CD4 T cell epitope identified in WNV. The mutant flavivirus E-glycoprotein polypeptides comprise an isoleucine at position 474, a threonine at position 484, a valine at position 488 and a leucine at position 493, each numbered with reference to the WNV E-glycoprotein polypeptide sequence, wherein the E-glycoprotein is from a flavivirus that is not WNV. In some embodiments, the flavivirus is DENV-2, DENV-1, DENV-3, DENV-4, Japanese encephalitis virus (JEV), Murray Valley encephalitis virus (MVEV), St. Louis encephalitis virus (SLEV), yellow fever virus (YFV) or tick-borne encephalitis virus (TBEV).

Also provided are virus-like particles (VLPs) comprising a disclosed mutant E-glycoprotein polypeptide. Further provided are recombinant nucleic acid molecules encoding one of the disclosed mutant E-glycoprotein polypeptides. Vectors comprising the recombinant nucleic acid molecules, and cells comprising such vectors, are also provided by the present disclosure.

Further provided are compositions comprising at least one of the disclosed mutant E-glycoprotein polypeptides, VLPs, recombinant nucleic acid molecules or vectors, and a pharmaceutically acceptable carrier.

Methods of eliciting an immune response in a subject against a flavivirus are further provided herein. In some embodiments, the method includes administering to the subject a therapeutically effective amount of a polypeptide, VLP, nucleic acid molecule, vector or composition as disclosed herein.

Also provided is a method of selecting a T cell epitope to enhance immunogenicity of a multivalent vaccine, wherein at least one component of the multivalent vaccine induces a weaker immune response compared with another component of the multivalent vaccine that induces a stronger immune response. In some embodiments, the method includes (i) performing peptide scanning on the vaccine components to identify positive (i.e. reactive) CD4 T cell epitopes or positive CD8 T cell epitopes, or both; (ii) comparing the positive T cell epitopes from the weaker vaccine component to the positive T cell epitopes from the stronger vaccine component to identify a candidate T cell epitope from the stronger vaccine component; and (iii) evaluating the ability of the candidate T cell epitope to bind human leukocyte antigen (HLA) alleles. The candidate T cell epitope is selected if it is capable of binding to multiple different HLA alleles.

Further provided is a method of enhancing immunogenicity of a multivalent vaccine, wherein at least one component of the multivalent vaccine induces a weaker immune response compared with another component of the multivalent vaccine that induces a stronger immune response, and wherein the method includes introducing the T cell epitope selected by the method disclosed herein into the weaker component of the multivalent vaccine.

The foregoing and other features and advantages will become more apparent from the following detailed description of several embodiments, which proceeds with reference to the accompanying figures.

BRIEF DESCRIPTION OF THE FIGURES

FIG. 4 is an amino acid alignment showing the transmembrane domain region is well conserved between WNV and JEV. Single letter amino acid abbreviations are shown for the transmembrane domain of WNV E protein using WNV numbering. Amino acids conserved relative to WNV in the other viruses are shown as dots, and single letter abbreviations for non-conserved amino acids are depicted. Four amino acids differ between residues 466 and 495 of WNV and JEV. Shown are the amino acid sequences of the TMD region of DENV-2 (DEN2; SEQ ID NO: 13), DENV-1 (DEN1; SEQ ID NO: 14), DENV-3 (DEN3; SEQ ID NO: 15), DENV-4 (DEN4; SEQ ID NO: 16), WNV (WN; SEQ ID NO: 17), JEV (JE; SEQ ID NO: 18), MVEV (MVE; SEQ ID NO: 19), SLEV (SLE; SEQ ID NO: 20), yellow fever virus (YF; SEQ ID NO: 21) and tickborn encephalitis virus (TBE; SEQ ID NO: 22).

SEQUENCE LISTING

Figure 1:
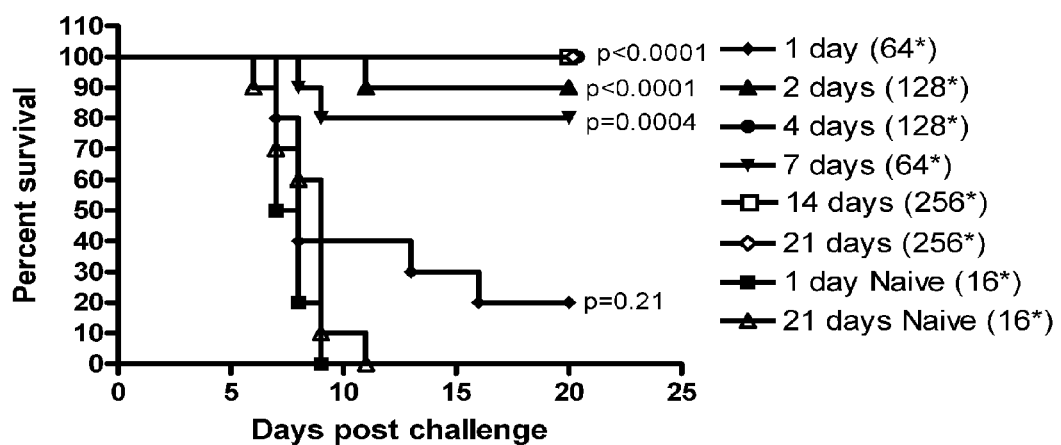
FIG. 1 is a line graph showing pVWNi elicits rapid protection from WNV challenge. Kaplan-Meier survival of vaccinated mice (n=10) challenged at 1, 2, 4, 7, 14, or 21 days post vaccination i.p. with 100,000 $LD_{50}$ WNV NY99. *$PRNT_{50}$ values of pooled group sera.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 23, 2013, 43.6 KB, which is incorporated by reference herein. In the accompanying sequence listing:

SEQ ID NOs: 1-4 are primer sequences.

SEQ ID NO: 5 is the amino acid sequence of residues 466-501 of the WNV E-glycoprotein TMD domain.

SEQ ID NO: 6 is the amino acid sequence of residues 466-495 of the WNV E-glycoprotein TMD domain, which includes a strong CD4 T cell epitope.

SEQ ID NO: 7 is the nucleic acid sequence of the DENV-2 RDERR construct containing the prM and E coding sequences.

SEQ ID NO: 8 is the amino acid sequence of the prM protein from DENV-2 RDERR.

SEQ ID NO: 9 is the amino acid sequence of the E-glycoprotein from DENV-2 RDERR.

SEQ ID NO: 10 is the nucleic acid sequence of the DENV-2 RDERR-TMD construct containing the prM and E coding sequences.

SEQ ID NO: 11 is the amino acid sequence of the prM protein from DENV-2 RDERR-TMD.

SEQ ID NO: 12 is the amino acid sequence of the E-glycoprotein from DENV-2 RDERR-TMD.

SEQ ID NO: 13 is a representative amino acid sequence of the TMD of the E-glycoprotein from DENV-2.

SEQ ID NO: 14 is a representative amino acid sequence of the TMD of the E-glycoprotein from DENV-1.

SEQ ID NO: 15 is a representative amino acid sequence of the TMD of the E-glycoprotein from DENV-3.

SEQ ID NO: 16 is a representative amino acid sequence of the TMD of the E-glycoprotein from DENV-4.

SEQ ID NO: 17 is a representative amino acid sequence of the TMD of the E-glycoprotein from WNV.

SEQ ID NO: 18 is a representative amino acid sequence of the TMD of the E-glycoprotein from JEV.

SEQ ID NO: 19 is a representative amino acid sequence of the TMD of the E-glycoprotein from MVEV.

SEQ ID NO: 20 is a representative amino acid sequence of the TMD of the E-glycoprotein from SLEV.

SEQ ID NO: 21 is a representative amino acid sequence of the TMD of the E-glycoprotein from YFV.

SEQ ID NO: 22 is a representative amino acid sequence of the TMD of the E-glycoprotein from TBEV.

SEQ ID NOs: 23-31 are amino acid sequences of mutant flavivirus E-glycoprotein polypeptides.

SEQ ID NOs: 32-37 are amino acid sequences of pVWNi and pVD2i E-glycoprotein peptides.

SEQ ID NO: 38 is the amino acid sequence of the WNV E-glycoprotein.

DETAILED DESCRIPTION

I. Abbreviations

BPL β-propiolactone
CRR cross-reactivity reduced
DENV dengue virus
DHF dengue hemorrhagic fever
DSS dengue shock syndrome
E flavivirus E protein
ELISA enzyme linked immunosorbent assay
FACS fluorescence activated cell sorting
FITC fluorescein isothiocyanate
FRμNT focus reduction microneutralization
HBsAg hepatitis B surface antigen
HBV hepatitis B virus
HPV human papilloma virus
ICS intracellular cytokine staining
IFN interferon
i.m. intramuscular
i.p. intraperitoneal
MLR mixed leukocyte reaction
JEV Japanese encephalitis virus
MVEV Murray Valley encephalitis virus
Nt. Ab. neutralizing antibody
OD optical density
PE phycoerythrin
prM premembrane protein
PRNT plaque reduction neutralization test
pv post vaccination
SEM standard error of the mean
SLEV St. Louis encephalitis virus
TBEV tick-borne encephalitis virus
TMD transmembrane domain
UV ultraviolet
VLP virus-like particle
WNV West Nile virus
WT wild type
YFV yellow fever virus II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218, 371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition (e.g. an immunogenic composition) to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Envelope glycoprotein (E protein): A flavivirus structural protein that mediates binding of flavivirus virions to cellular receptors on host cells. The flavivirus E protein is required for membrane fusion, and is the primary antigen inducing protective immunity to flavivirus infection. Flavivirus E protein affects host range, tissue tropism and viral virulence. The flavivirus E protein contains three structural and functional domains, DI-DIII. In mature virus particles the E protein forms head to tail homodimers lying flat and forming a dense lattice on the viral surface. Non-limiting examples of E proteins from various flaviviruses are provided herein.

Immune response: A response of a cell of the immune system, such as a B-cell, T-cell, macrophage or polymorphonucleocyte, to a stimulus such as an antigenic polypeptide or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immune stimulatory composition: A term used herein to mean a composition useful for stimulating or eliciting a specific immune response (or immunogenic response) in a subject. The immune stimulatory composition can be a protein antigen or a nucleic acid molecule (such as vector) used to express a protein antigen. In some embodiments, the immunogenic response is protective or provides protective immunity, in that it enables the subject to better resist infection with or disease progression from the flavivirus against which the immune stimulatory composition is directed.

In some embodiments, an "effective amount" or "immune-stimulatory amount" of an immune stimulatory composition is an amount which, when administered to a subject, is sufficient to engender a detectable immune response. Such a response may comprise, for instance, generation of an antibody specific to one or more of the epitopes provided in the immune stimulatory composition. Alternatively, the response may comprise a T-helper or CTL-based response to one or more of the epitopes provided in the immune stimulatory composition. All three of these responses may originate from naïve or memory cells. In other embodiments, a "protective effective amount" of an immune stimulatory composition is an amount which, when administered to a subject, is sufficient to confer protective immunity upon the subject.

Immunogen: A compound, composition, or substance which is capable, under appropriate conditions, of stimulating an immune response, such as the production of antibodies or a T-cell response in an animal, including compositions that are injected or absorbed into an animal. In some embodiments of the present disclosure, an "immunogenic composition" is a composition comprising a mutant E-glycoprotein polypeptide.

Immunize: To render a subject protected from an infectious disease, such as by vaccination.

Isolated: An "isolated" or "purified" biological component (such as a nucleic acid, peptide, protein, protein complex, or virus-like particle) has been substantially separated, produced apart from, or purified away from other biological components in the cell of the organism in which the component naturally occurs, that is, other chromosomal and extra-chromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Mutant: In the context of the present disclosure, a "mutant" flavivirus E-glycoprotein is a flavivirus E-glycoprotein having one or more amino acid substitutions such that the positions of the mutant polypeptide corresponding to residues 474, 484, 488 and 493 of the WNV E-glycoprotein (SEQ ID NO: 38) are an isoleucine, a threonine, a valine and a leucine, respectively. The mutant flavivirus E-glycoprotein can optionally contain additional mutations (such as insertions, deletions or other substitutions) so long as the polypeptide retains antigenicity and the ability to form VLPs when co-expressed with the prM protein.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more flavivirus vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

A conservative substitution in a polypeptide is substitution of one amino acid residue in a protein sequence for a different amino acid residue having similar biochemical properties. Typically, conservative substitutions have little to no impact on the activity of a resulting polypeptide. For example, a flavivirus protein including one or more conservative substitutions (for example no more than 2, 5, 10, 20, 30, 40, or 50 substitutions) retains the structure and function of the wild-type protein. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Premembrane protein (prM protein): A flavivirus structural protein. The prM protein is an approximately 25 kDa protein that is the intracellular precursor for the membrane (M) protein. prM is believed to stabilize the E protein during transport of the immature virion to the cell surface. When the virus exits the infected cell, the prM protein is cleaved to the mature M protein, which is part of the viral envelope (Reviewed in Lindenbach and Rice, In: *Fields Virology*, Knipe and Howley, eds., Lippincott, Williams, and Wilkins, 991-1041, 2001).

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of one or more signs or symptoms of a disease.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some embodiments herein, the promoter is suitable for expression in yeast cells.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. The term recombinant includes nucleic acids, proteins and viruses that have been altered solely by addition, substitution, or deletion of a portion of a natural nucleic acid molecule, protein or virus.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:

403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Subject: Living multi-cellular vertebrate organisms, a category that includes both human and non-human mammals (such as mice, rats, rabbits, sheep, horses, cows, and non-human primates).

Therapeutically effective amount: A quantity of a specified agent (such as an immunogenic composition) sufficient to achieve a desired effect in a subject being treated with that agent. For example, this may be the amount of a virus vaccine useful for eliciting an immune response in a subject and/or for preventing infection by the virus. In the context of the present disclosure, a therapeutically effective amount of a flavivirus vaccine, for example, is an amount sufficient to increase resistance to, prevent, ameliorate, and/or treat infection caused by a flavivirus in a subject without causing a substantial cytotoxic effect in the subject. The effective amount of a flavivirus immune stimulating composition useful for increasing resistance to, preventing, ameliorating, and/or treating infection in a subject will be dependent on, for example, the subject being treated, the manner of administration of the therapeutic composition and other factors.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins (including VLPs), peptides or DNA derived from them. An attenuated vaccine is a virulent organism that has been modified to produce a less virulent form, but nevertheless retains the ability to elicit antibodies and cell-mediated immunity against the virulent form. A killed vaccine is a previously virulent microorganism that has been killed with chemicals or heat, but elicits antibodies against the virulent microorganism. Vaccines may elicit both prophylactic (preventative) and therapeutic responses. Methods of administration vary according to the vaccine, but may include inoculation, ingestion, inhalation or other forms of administration. Vaccines may be administered with an adjuvant to boost the immune response. In some embodiments of the present the disclosure, the vaccine comprises a heterologous CD4 T cell epitope to enhance immunogenicity of the vaccine. For example, a polypeptide-based vaccine can be engineered to include the CD4 T cell epitope peptide sequence. As another example, a DNA vaccine can include a nucleic acid sequence encoding the CD4 T cell epitope.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes.

Virus-like particle (VLP): Virus particles made up of one of more viral structural proteins, but lacking the viral genome. Because VLPs lack a viral genome, they are non-infectious. In some embodiments, the VLPs are flavivirus VLPs. In particular examples, the flavivirus VLPs include two flavivirus structural proteins—prM and E.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

The development and protective efficacy of a West Nile virus (WNV) DNA vaccine directing the expression of pre-membrane and envelope (prM/E) proteins has been previously described. A single 100 µg intramuscular (i.m.) injection of WNV DNA vaccine in mice induced a high level of WNV neutralizing antibodies and protected 100% of mice challenged by either intraperitoneal (i.p.) or mosquito inoculation (Davis et al., *J Virol* 75(9): 4040-4047, 2001). In addition, a single i.m. injection of WNV DNA vaccine protected vaccinated horses from viremia by mosquito inoculation. In comparison, for the previously described DENV-2 DNA vaccine, two i.m. vaccinations of 100 µg were required to elicit a high enough neutralizing antibody titer to passively protect neonatal mice from challenge (Chang et al., *Virology* 306(1): 170-180, 2003). Both DNA vaccines contain identical enhancer, promoter, translational control element and JEV signal sequence (Chang et al., *J Virol* 74(9): 4244-4252, 2000); however, the difference in immunogenicity of the two vaccines is striking. Moreover, three days post vaccination of 100 µg of WNV DNA vaccine, 100% of mice were protected from virus challenge, suggesting a rapid cell mediated and innate immune response to the vaccine. These observations led to the hypothesis of differential antigenic determinants between the WNV and DENV-2 DNA vaccines, potentially involving the cellular mediated arm of the immune system. Described herein is the identification and application of a potent WNV CD4 positive T cell epitope to increase the immunogenicity of DENV-2 DNA and virus-like particle (VLP) vaccines, as well as other heterologous vaccines (including any other flavivirus). In addition, the methods disclosed herein can be applied to the identification of other potent T cell epitopes to enhance immunogenicity of other vaccines.

IV. Overview of Several Embodiments

Provided by the present disclosure are mutant flavivirus E-glycoprotein polypeptides that contain the potent CD4 T cell epitope identified in the TMD of the E-glycoprotein of WNV. In particular, the mutant polypeptides each include an isoleucine at position 474, a threonine at position 484, a valine at position 488 and a leucine at position 493, each numbered with reference to the wild-type WNV E-glycoprotein sequence.

In some embodiments, provided is an isolated mutant flavivirus E-glycoprotein polypeptide, wherein the polypeptide comprises an isoleucine at position 474, a threonine at position 484, a valine at position 488 and a leucine at position 493, each numbered with reference to the West Nile virus E-glycoprotein polypeptide sequence of SEQ ID NO: 38, wherein the flavivirus is not West Nile virus. In some examples, the flavivirus is DENV-2, DENV-1, DENV-3, DENV-4, Japanese encephalitis virus (JEV), Murray Valley encephalitis virus (MVEV), St. Louis encephalitis virus (SLEV), yellow fever virus (YFV) or tick-borne encephalitis virus (TBEV). In one non-limiting example, the flavivirus is DENV-2.

In some examples, the amino acid sequence of the polypeptide is at least 95%, at least 96%, at least 97%, at least 98% or at least 99% identical to SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31, while retaining an isoleucine at position 474, a threonine at position 484, a valine at position 488 and a leucine at position 493 relative to the WNV E-glycoprotein sequence of SEQ ID NO: 38.

In specific examples, the amino acid sequence of the polypeptide comprises SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31.

In other examples, the amino acid sequence of the polypeptide is at least 95%, at least 96%, at least 97%, at least 98% or at least 99% identical to SEQ ID NO: 12, while retaining an isoleucine at position 474, a threonine at position 484, a valine at position 488 and a leucine at position 493 relative to the WNV E-glycoprotein sequence of SEQ ID NO: 38. In specific examples, the amino acid sequence of the polypeptide comprises or consists of SEQ ID NO: 12.

Also provided herein are isolated VLPs containing a mutant flavivirus E-glycoprotein polypeptide disclosed herein. In some embodiments, the VLP further comprises a prM protein. The VLP can optionally further include the C protein.

Further provided are recombinant nucleic acid molecules encoding a mutant flavivirus E-glycoprotein polypeptide, or encoding a VLP containing a mutant flavivirus E-glycoprotein polypeptide. In particular examples, the recombinant nucleic acid molecule is at least 95%, at least 96%, at least 97%, at least 98% or at least 99% identical to SEQ ID NO: 10. In one non-limiting example, the recombinant nucleic acid molecule comprises the nucleotide sequence of SEQ ID NO: 10.

Also provided are vectors comprising the recombinant nucleic acid molecules disclosed herein, and isolated cells comprising such vectors.

Compositions, such as immune stimulating compositing, are further provided by the present disclosure. In some embodiments, the compositions include a mutant flavivirus E-glycoprotein polypeptide, a VLP comprising a mutant flavivirus E-glycoprotein polypeptide, a recombinant nucleic acid molecule encoding a mutant flavivirus E-glycoprotein polypeptide or a VLP comprising the mutant polypeptide, or a vector encoding a mutant flavivirus E-glycoprotein polypeptide or a VLP comprising the mutant polypeptide, and a pharmaceutically acceptable carrier. In some embodiments, the composition further includes an adjuvant.

The present disclosure also provides methods of eliciting an immune response in a subject against a flavivirus. In some embodiments, the method includes administering to the subject a therapeutically effective amount of a polypeptide, VLP, nucleic acid molecule, vector or composition as disclosed herein. In some embodiments, the subject is a mammal, such as a human.

Also provided is a method of selecting a T cell epitope to enhance immunogenicity of a multivalent vaccine, wherein at least one component of the multivalent vaccine induces a weaker immune response compared with another component of the multivalent vaccine that induces a stronger immune response. In some embodiments, the method includes (i) performing peptide scanning on the vaccine components to identify positive CD4 T cell epitopes or positive CD8 T cell epitopes, or both; (ii) comparing the positive T cell epitopes from the weaker vaccine component to the positive T cell epitopes from the stronger vaccine component to identify a candidate T cell epitope from the stronger vaccine component; and (iii) evaluating the ability of the candidate T cell epitope to bind human HLA alleles. The candidate T cell epitope is selected if it is capable of binding to multiple different HLA alleles. In some embodiments, the T cell epitope is a CD4 T cell epitope. In other embodiments, the T cell epitope is a CD8 T cell epitope. In some embodiments, the multivalent vaccine is a trivalent or tetravalent vaccine.

Further provided is a method of enhancing immunogenicity of a multivalent vaccine, wherein at least one component of the multivalent vaccine induces a weaker immune response compared with another component of the multivalent vaccine that induces a stronger immune response. In some embodiments, the method includes introducing the T cell epitope selected by the method disclosed herein into the weaker component of the multivalent vaccine. In some embodiments, the T cell epitope is a CD4 T cell epitope. In other embodiments, the T cell epitope is a CD8 T cell epitope. In some embodiments, the multivalent vaccine is a trivalent or tetravalent vaccine.

V. Mutant Flavivirus E-Glycoprotein Polypeptides

Provided by the present disclosure are mutant flavivirus E-glycoprotein polypeptides that contain the potent CD4 T cell epitope identified in the TMD of the E-glycoprotein of WNV. In particular, the mutant polypeptides each include an isoleucine at position 474, a threonine at position 484, a valine at position 488 and a leucine at position 493, each numbered with reference to the WNV E-glycoprotein polypeptide sequence of SEQ ID NO: 38. In other words, the mutant E-glycoproteins include an isoleucine at a position that corresponds to residue 474 of the WNV E-glycoprotein, a threonine at a position that corresponds to residue 484 of the WNV E-glycoprotein, a valine at a position that corresponds to residue 488 of the WNV E-glycoprotein and a leucine at a position that corresponds to residue 493 of the WNV E-glycoprotein. One of skill in the art will understand that variations in the sequences and amino acid positions of E-glycoproteins of different flaviviruses exist, and can determine what mutant E-glycoproteins are encompassed by the present disclosure.

The amino acid sequences of the TMD of selected flaviviruses are shown below. In both the wild-type (WT) and mutant sequences, the positions corresponding to residues 474, 484, 488 and 493 of WNV (SEQ ID NO: 38) are underlined. In each mutant sequence, the positions corresponding to residues 474, 484, 488 and 493 of WNV are an isoleucine, a threonine, a valine and a leucine, respectively.

DENV-2 WT
(SEQ ID NO: 13)
LGDTAWDFGSLGGVFTSIGKALHQVFGAIYGAAFSGVSWTMKILIGVIIT
WIGMNSRSTSLSVSLVLVGVVTLYLGAMVQA

DENY-1 WT
(SEQ ID NO: 14)
LGDTAWDFGSIGGVFTSVGKLIHQIFGTAYGVLFSGVSWTMKIGIGILLT
WLGLNSRSTSLSMTCIAVGMVTLYLGVMVQA

DENV-3 WT
(SEQ ID NO: 15)
LGDTAWDFGSVGGVLNSLGKMVHQIFGSAYTALFSGVSWIMKIGIGVLLT
WIGLNSKNTSMSFSCIAIGIITLYLGVVVQA

DENV-4 WT
(SEQ ID NO: 16)
LGETAWDFGSVGGLFTSLGKAVHQVFGSVYTTMFGGVSWMIRILIGFLVL
WIGTNSRNTSMAMTCIAVGGITLFLGFTVQA

WNV WT
(SEQ ID NO: 17)
LGDTAWDFGSVGGVFTSVGKAVHQVFGGAFRSLFGGMSWITQGLLGALLL
WMGINARDRSIALTFLAVGGVLLFLSVNVHA

JEV WT
(SEQ ID NO: 18)
LGDTAWDFGSIGGVFNSIGKAVHQVFGGAFRTLFGGMSWITQGLMGALLL
WMGVNARDRSIALAFLATGGVLVFLATNVHA

MVEV WT
(SEQ ID NO: 19)
LGDTAWDFGSVGGVFNSIGKAVHQVFGGAFRTLFGGMSWISPGLLGALLL
WMGVNARDKSIALAFLATGGVLLFLATNVHA

SLEV WT
(SEQ ID NO: 20)
LGDTAWDFGSIGGVFNSIGKAVHQVFGGAFRTLFGGMSWITQGLLGALLL
WMGLQARDRSISLTLLATGGILIFLATSVQA

YFV WT
(SEQ ID NO: 21)
MGDAAWDFSSAGGFFTSVGKGIHTVFGSAFQGLFGGLNWITKVIMGAVLI
WVGINTRNMTMSMSMILVGVIMMFLSLGVGA

TBEV WT
(SEQ ID NO: 22)
IGEHAWDFGSAGGFLSSIGKAVHTVLGGAFNSIFGGVGFLPKLLLGVALA
WLGLNMRNPTMSMSFLLAGGLVLAMTLGVGA

DENV-2 Mutant
(SEQ ID NO: 23)
LGDTAWDFGSLGGVFTSIGKALHQVFGAIYGAAFSGVSWTMKILIGVIIT
WIGINSRSTSLSVTLVLVGVVTLYLGAMVQA DENV-1 Mutant
(SEQ ID NO: 24)
LGDTAWDFGSIGGVFTSVGKLIHQIFGTAYGVLFSGVSWTMKIGIGILLT
WLGINSRSTSLSMTCIAVGMVTLYLGVMVQA DENV-3 Mutant
(SEQ ID NO: 25)
LGDTAWDFGSVGGVLNSLGKMVHQIFGSAYTALFSGVSWIMKIGIGVLLT
WIGINSKNTSMSFTCIAVGIITLYLGVVVQA DENV-4 Mutant
(SEQ ID NO: 26)
LGETAWDFGSVGGLFTSLGKAVHQVFGSVYTTMFGGVSWMIRILIGFLVL
WIGINSRNTSMAMTCIAVGGITLFLGFTVQA JEV Mutant
(SEQ ID NO: 27)
LGDTAWDFGSIGGVFNSIGKAVHQVFGGAFRTLFGGMSWITQGLMGALLL
WMGINARDRSIALTFLAVGGVLLFLATNVHA MVEV Mutant
(SEQ ID NO: 28)
LGDTAWDFGSVGGVFNSIGKAVHQVFGGAFRTLFGGMSWISPGLLGALLL
WMGINARDKSIALTFLAVGGVLLFLATNVHA SLEV Mutant
(SEQ ID NO: 29)
LGDTAWDFGSIGGVFNSIGKAVHQVFGGAFRTLFGGMSWITQGLLGALLL
WMGIQARDRSISLTLLAVGGILLFLATSVQA YFV Mutant
(SEQ ID NO: 30)
MGDAAWDFSSAGGFFTSVGKGIHTVFGSAFQGLFGGLNWITKVIMGAVLI
WVGINTRNMTMSMTMILVGVIMLFLSLGVGA TBEV Mutant
(SEQ ID NO: 31)
IGEHAWDFGSAGGFLSSIGKAVHTVLGGAFNSIFGGVGFLPKLLLGVALA
WLGINMRNPTMSMTFLLVGGLVLAMTLGVGA Also provided by the present disclosure are VLPs comprising the mutant flavivirus E-glycoprotein polypeptides. Generally, flavivirus VLPs are made up of the prM and E proteins, but can also include the C protein. The production of flavivirus VLPs has been described in the art and is within the abilities of one of ordinary skill in the art. For example, flavivirus VLPs can be produced by transfection of host cells with a plasmid encoding the prM and E proteins (and optionally the C protein). After incubation of the transfected cells for an appropriate time to allow for protein expression, VLPs can be isolated from cell culture supernatants according to standard procedures (see Example 1 for an exemplary method).

VI. Immunostimulatory Compositions and Administration Thereof

The immunostimulatory compositions provided herein can include, for example, a mutant flavivirus E-glycoprotein polypeptide, a recombinant nucleic acid molecule encoding a mutant flavivirus E-glycoprotein polypeptide, a VLP comprising a mutant flavivirus E-glycoprotein polypeptide, or a recombinant nucleic acid molecule (such as a vector) encoding a VLP.

The mutant flavivirus E-glycoprotein polypeptides and VLPs (including nucleic acid molecules encoding the mutant polypeptides and VLPs) disclosed herein can be used as flavivirus vaccines to elicit an immune response, such as a protective immune response, against flavivirus.

The provided immunostimulatory flavivirus polypeptides, constructs or vectors encoding such polypeptides, are combined with a pharmaceutically acceptable carrier or vehicle for administration as an immune stimulatory composition to human or animal subjects. In a particular embodiment, the immune stimulatory composition administered to a subject directs the synthesis of a mutant flavivirus E-glycoprotein as described herein, and a cell within the body of the subject, after incorporating the nucleic acid within it, secretes VLPs comprising the mutant E-glycoprotein. It is believed that such VLPs then serve as an in vivo immune stimulatory composition, stimulating the immune system of the subject to generate protective immunological responses. In some embodiments, more than one immune stimulatory flavivirus polypeptide, construct or vector may be combined to form a single preparation.

The immunogenic formulations may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immune stimulatory compositions, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes.

The volume of administration will vary depending on the route of administration. By way of example, intramuscular injections may range from about 0.1 ml to about 1.0 ml. Those of ordinary skill in the art will know appropriate volumes for different routes of administration.

Immune stimulatory compounds (for example, vaccines) can be administered by directly injecting nucleic acid molecules encoding peptide antigens (broadly described in Janeway & Travers, *Immunobiology: The Immune System In Health and Disease*, page 13.25, Garland Publishing, Inc., New York, 1997; and McDonnell & Askari, *N. Engl. J. Med.* 334:42-45, 1996). Vectors that include nucleic acid molecules described herein, or that include a nucleic acid sequence encoding a mutant E-glycoprotein flavivirus polypeptide may be utilized in such DNA vaccination methods.

Thus, the term "immune stimulatory composition" as used herein also includes nucleic acid vaccines in which a nucleic acid molecule encoding a mutant flavivirus E-glycoprotein polypeptide is administered to a subject in a pharmaceutical composition. For genetic immunization, suitable delivery methods known to those skilled in the art include direct injection of plasmid DNA into muscles (Wolff et al., *Hum. Mol. Genet.* 1:363, 1992), delivery of DNA complexed with specific protein carriers (Wu et al., *J. Biol. Chem.* 264:16985, 1989), co-precipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992; Eisenbraun et al., *DNA Cell Biol.* 12:791, 1993), and in vivo infection using cloned retroviral vectors (Seeger et al., *Proc. Natl. Acad. Sci.* 81:5849, 1984). Similarly, nucleic acid vaccine preparations can be administered via viral carrier.

The amount of immunostimulatory compound in each dose of an immune stimulatory composition is selected as an amount that induces an immunostimulatory or immunoprotective response without significant, adverse side effects. Such amount will vary depending upon which specific immunogen is employed and how it is presented. Initial injections may range from about 1 µg to about 1 mg, with some embodiments having a range of about 10 µg to about 800 µg, and still other embodiments a range of from about 25 µg to about 500 µg. Following an initial administration of the immune stimulatory composition, subjects may receive one or several booster administrations, adequately spaced. Booster administrations may range from about 1 µg to about 1 mg, with other embodiments having a range of about 10 µg to about 750 µg, and still others a range of about 50 µg to about 500 µg. Periodic boosters at intervals of 1-5 years, for instance three years, may be desirable to maintain the desired levels of protective immunity.

Flavivirus polypeptides or VLPs (or nucleic acid molecules encoding flavivirus polypeptides or VLPs), or compositions thereof, are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Particular methods for administering nucleic acid molecules are well known in the art. In some examples, the nucleic acid encoding the flavivirus polypeptide or VLP is administered by injection (such as intramuscular or intradermal injection) or by gene gun.

Administration can be accomplished by single or multiple doses. The dose administered to a subject in the context of the present disclosure should be sufficient to induce a beneficial therapeutic response in a subject over time, or to inhibit or prevent flavivirus infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation.

It is also contemplated that the provided immunostimulatory molecules and compositions can be administered to a subject indirectly, by first stimulating a cell in vitro, which stimulated cell is thereafter administered to the subject to elicit an immune response. Additionally, the pharmaceutical or immune stimulatory compositions or methods of treatment may be administered in combination with other therapeutic treatments. For example, the compositions provided herein can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

VII. Method of Enhancing Immunogenicity of a Vaccine

Described herein is a method of identifying a strong T cell epitope and its use in a heterologous vaccine to enhance immunogenicity of the vaccine. This method is exemplified by the identification of a strong T cell epitope in the E-glycoprotein of WNV, which is not present in the E-glycoprotein of the DENV-2 vaccine (pVD2i). Incorporation of the WNV T cell epitope into the DENV-2 vaccine significantly improved immunogenicity of the DENV-2 vaccine (see Example 2 below). However, this method can be applied to any multivalent vaccine in which one component of the vaccine is weaker than another component of the vaccine.

Thus, provided herein is a method of selecting a T cell epitope to enhance immunogenicity of a multivalent vaccine, wherein at least one component of the multivalent vaccine induces a weaker immune response compared with another component of the multivalent vaccine that induces a stronger immune response. In some embodiments, the method includes:

(i) performing peptide scanning on the vaccine components to identify positive CD4 T cell epitopes or positive CD8 T cell epitopes, or both;

(ii) comparing the positive T cell epitopes from the weaker vaccine component to the positive T cell epitopes from the stronger vaccine component to identify a candidate T cell epitope from the stronger vaccine component; and (iii) evaluating the ability of the candidate T cell epitope to bind human HLA alleles, wherein the candidate T cell epitope is selected if it is capable of binding to multiple different HLA alleles.

Methods of peptides scanning have been well described in the art and are well within the capabilities of one of skill in the art (see, for example, Kern et al., *Eur J Immunol* 30(6): 1676-1682, 2000; Betts et al., *J Virol* 75(24): 11983-91, 2001; Maecker et al., *J Immunol Methods* 255(1-2): 27-40, 2001; or Hoffmeister et al., *Methods* 29(3): 270-281, 2003). In some examples, peptide scanning includes generating a library of short peptides (such as peptides 10, 11, 12, 13, 14, 15, 16, 17, 18, 19 or 20 amino acids in length) corresponding to the weak component of the vaccine and another library of peptides that corresponds to the strong component of the vaccine. The "component" of the vaccine is generally the immunogenic component of the vaccine, such as a protein antigen. The peptides optionally have small overlaps with each other, such as 3, 4, 5, 6, 7, 8, 9, 10, 11, 12, 13, 14 or 15 amino acid overlaps. In particular examples, the peptide libraries consist of 15mer peptides with 10 amino acid overlaps.

In some examples, the peptides are arranged in pools (as described in Example 2, or as described previously by Kern et al., *Eur J Immunol* 30(6): 1676-1682, 2000; Betts et al., *J Virol* 75(24): 11983-91, 2001; Maecker et al., *J Immunol Methods* 255(1-2): 27-40, 2001; or Hoffmeister et al., *Methods* 29(3): 270-281, 2003), and the individual peptides are identified by pool overlap. Selected individual peptides can optionally go through a second round of screening.

Positive peptides can be selected using any appropriate method. In some embodiments, positive peptides are confirmed by ex vivo stimulation of splenocytes from vaccinated individuals. Positive peptides will generally lead to IFNγ expression by CD4+ and/or CD8+ cells.

Evaluating the ability of the candidate T cell epitope to bind human HLA alleles can be performed, for example, using ProPed and ProPedI to identify CD8 and CD4 T cell epitopes, respectively, with the potential to bind human HLA alleles. The candidate T cell epitope is selected if it is capable of binding to multiple different HLA alleles. In some embodiments, the ability to bind multiple different HLA alleles is a determination based on the percentage of HLA alleles to which the epitope is capable of binding. In some examples, the T cell epitope is selected if it is capable of binding to at least 20%, at least 30%, at least 40%, at least 50%, at least 60%, at least 70%, at least 80%, at least 90, or at least 95% of human HLA alleles evaluated. In other embodiments, the ability of the T cell epitope to bind multiple different HLA alleles is determined by the number of HLA alleles to which the epitope can bind. In some examples, the T cell epitope is selected if it is capable of binding to at least 10, at least 15, at least 20, at least 25, at least 30, at least 35, at least 40, at least 45, or at least 50 different human HLA alleles.

Further provided is a method of enhancing immunogenicity of a multivalent vaccine, wherein at least one component of the multivalent vaccine induces a weaker immune response compared with another component of the multivalent vaccine that induces a stronger immune response. In some embodiments, the method includes introducing the T cell epitope selected by the method described above into the weaker component of the multivalent vaccine. In some examples, "introducing" the T cell epitope involves changing specific amino acids such that the epitope sequence is present in the weaker vaccine component following the amino acid modifications. In other examples, "introducing" the T cell epitope includes cloning the T cell epitope into the weaker vaccine component.

In some embodiments of the methods, the T cell epitope is a CD4 T cell epitope. In other embodiments, the T cell epitope is a CD8 T cell epitope.

In some embodiments, the multivalent vaccine is a trivalent vaccine. In other embodiments, the vaccine is a tetravalent vaccine.

In particular examples, the vaccine is a HPV vaccine. In one non-limiting example, the vaccine is a trivalent HPV vaccine for serotypes 16/18/58.

The following examples are provided to illustrate certain particular features and/or embodiments. These examples should not be construed to limit the disclosure to the particular features or embodiments described.

EXAMPLES

Example 1

Materials and Methods

This example describes the experimental procedures for the studies described in Example 2.

Vaccines

Construction and characterization of pVWNi, DENV-2 DNA plasmid optimized with C terminal 20% JEV, and pVD2i with substitutions in the E domain II FP and EDIII have been previously described (Chang et al., *Virology* 306 (1):170-180, 2003; Davis et al., *J Virol* 75(9): 4040-4047, 2001; Crill et al., *PLoS ONE* 4(4):e991, 2009; Chang et al., *Vaccine* 25: 12:2325-2330, 2007). pVWNi, pVD2i (WT) and pVD21G106R/L107D/K310E/E311R/P364R (RDERR) were manufactured by Aldevron (Fargo, N. Dak.). pVD2i with substitutions in the transmembrane domain, pVD21V474I, pVD21V474I/A484T, pVD21V474I/A484T/T488V, and pVD21V474I/A484T/T488V/V493L (WT-TMD), were generated by using Quick change site-directed mutagenesis kit (Stratagene) sequentially with the following primers (Operon):

```
                                              (SEQ ID NO: 1)
3'CGGGATGACGAGACCTACCCGTATTTGCGTGCTCTG5', (SEQ ID NO: 2)
3'GCTAGTTACGAAACTGGAAGAATCGGTGTCCCCCACAC5', (SEQ ID NO: 3)
3'CTGGAAGAATCGGCATCCCCCACACGAGCACAAG5',
and (SEQ ID NO: 4)
3'CCCCCACACGAGGACAAGAATCGCTGGTTACACG5'.
``` pVD21G106R/L107D/K310E/E311R/P364R/V474I/A484T/T488V/V493L (RDERR-TMD) was generated by restriction enzyme cloning by digesting pVD21V474I/A484T/T488V/V493L (WT-TMD) with KpnI and StuI (New England Biolabs), and Quick ligation (New England Biolabs) of the transmembrane domain region into the pVD21G106R/L107D/K310E/E311R/P364R backbone. WT-TMD and RDERR-TMD were grown in *E. coli* XL1 Blue cells and DNA purified for vaccination by ENDOFREE™ Plasmid Maxi-prep Kit (Qiagen) as per manufacturer's instructions. Structural gene elements and regulatory elements of all plasmids were sequenced entirely upon identification of the correct mutation. Automated DNA sequencing was performed using a Beckman Coulter CEQ 8000 genetic analysis system (Beckman Coulter) and analyzed by using Beckman Coulter CEQ 8000 (Beckman Coulter) and Lasergene software (DNASTAR).

Virus-like particles (VLPs) were generated by transformation of COS-1 cells as previously described (Chang et al., *J Virol* 74(9):4244-4252, 2000) and secreted VLPs were harvested from serum and animal product free media (Sfm4 megavir (Hyclone) supplemented with L-glutamine, non-essential amino acids, penicillin-streptomycin, sodium pyruvate, and cholesterol (Gibco)). Tissue culture media was harvested 4 days post transformation, pelleted by ultracentrifugation at 19,000 rpm, concentrated 100-fold in TN buffer, pelleted by 20% sucrose cushion, and resuspended in 1/100 of original volume in TN buffer. Protein concentration was determined by Bradford Assay (BioRad) as per manufacturer's instructions. Final VLP vaccines consisted of 1 µg protein in 8% Alum (Thermo Scientific).

Mice

C57BL/6J mice were purchased from Jackson Laboratory. Swiss Webster mice were purchased from Charles River. All mice were immunized i.m. with 100 µg of DNA or 1 µg of VLPs formulated with 8% Alum (Thermo Scientific). C57BL/6 mice were immunized with pVWNi on day 0 and challenged with 100,000 $LD_{50}$ WNV NY99 i.p. on days 1, 2, 4, 7, 14, or 21 post vaccination (n=10). C57BL/6 mice were immunized with pVWNi on day 0 and sacrificed on days 2, 4, 7, and 14 (n=5), AND muscles, inguinal lymph nodes and spleens collected. C57BL/6J mice were immunized with pVWNi or pVD2i on weeks 0, boosted on week 3, sacrificed and splenectomized on week 6. C57BL/6J mice were immunized with pVD2i TMD constructs at weeks 0 and 4, sacrificed on week 8, splenectomized and serum collected. Swiss Webster mice were similarly immunized and sacrificed on week 12, splenectomized and serum collected. Swiss Webster mice were immunized with VLP on weeks 0 and 4, sacrificed on week 8, splenectomized and serum collected. Animal experiments were approved by IACUC.

Histology

Mice were euthanized on days 4 and 7 post vaccination and the tibialis muscle removed. Tissue samples were fixed in 4% buffered formalin solution and sent to Colorado State Diagnostic Laboratories for slide preparation and Hematoxylin and Eosin (H&E) staining. Slides were viewed on a Zeiss microscope, and all images were taken at 600× magnification.

Peptide Scanning Library

A library of 15 amino acid peptides with 10 amino acid overlaps was designed to cover either the envelope (E) protein or the pre-membrane (prM) region of WNV or DENV-2 (AC Scientific, Inc.). Peptides were arranged in pools as described previously (Kern et al., *Eur J Immunol* 30(6): 1676-1682, 2000; Betts et al., *J Virol* 75(24): 11983-91, 2001; Maecker et al., *J Immunol Methods* 255(1-2): 27-40, 2001; Hoffmeister et al., *Methods* 29(3): 270-281, 2003). Single peptides were used at a concentration of 1 µg/ml with the total concentration of each pool being no greater than 10 µg/ml (Kern et al., *Eur J Immunol* 30(6): 1676-1682, 2000; Betts et al., *J Virol* 75(24): 11983-91, 2001; Maecker et al., *J Immunol Methods* 255(1-2): 27-40, 2001). Pool volumes were diluted in such a manner that the DMSO concentration is no greater than 1% of v/v (Hoffmeister et al., *Methods* 29(3): 270-281, 2003). Individual peptides were identified by pool overlap. The selected individual peptides went through a second round of screening. Positive peptides were determined by ex vivo stimulation of splenocytes from vaccinated animals and demonstrated CD4+ and/or CD8+ and levels of IFN-γ expression.

Epitope prediction of positive peptides was accomplished using online prediction engines ProPedI (available online at imtech.res.in/raghava/propred1/) and ProPed (available online at imtech.res.in/raghava/propred/) setting the threshold to the most stringent 1%. Helical wheel projections of peptides were generated using BioEdit (available online at mbio.ncsu.edu/bioedit/bioedit.html).

Mixed Leukocyte Reactions

Single cell suspensions were made from freshly harvested C57BL/6J or Swiss Webster spleens and plated in 96-well plates for extracellular surface antigen and intracellular cytokine staining (ICS). Splenocytes were stimulated with peptides as described above or 2 µg of UV inactivated DENV or rWNV-E (expressed in *Drosophila melanogaster* S2 cells); PHA (Roche Diagnostics) was used as a positive control, and naïve splenocytes in cell culture medium as negative controls. 96-well plates were incubated 2 hours and 1 µg of Golgi plug (BD Biosciences) was added to each well, and plates were incubated an additional 4 hours before extracellular and intracellular staining.

Flow Cytometry

The antibodies mouse BD Fc block, CD3, CD4, CD8, CD11b, F4/80, CD19, B220, CD80, CD28, CD154, IFNγ, TNFα, IL-2, IL-4, and IL-5 were purchased from BD Biosciences or eBiosciences. Stimulated splenocytes were centrifuged, washed with BD Stain buffer (BD Biosciences), Fc blocked, and labeled for extracellular antigens: CD3, CD4, CD8, CD11b, F4/80, CD19, B220, CD80, CD28, or CD154. For intracellular staining CD3+/CD4+ splenocytes were then fixed with BD cytofix/cytoperm buffer (BD Biosciences) and labeled for IFNγ, TNFα, IL-2, IL-4, or IL-5. For WNV and peptide library work, cells were analyzed using a High Performance MoFlo™ Cell Cytometer/Sorter and Summit version 3 software (DakoCytomation, Fort Collins, Colo.). Cells were gated on the small lymphocyte or CD3 positive population and 10,000 events were collected. For transmembrane domain replacement studies, fluorescence was detected with BD FACS Calibur and Cell quest software (BD Biosciences). The lymphocyte population was gated on a FSC and SSC plot and further gated on CD3 and CD4 or CD8 and 40,000 gated events were collected and analyzed for FITC and PE positive cells. Double-positive cells from the negative control were subtracted from each sample before statistical analysis. Dot plots are representative of a single replicate.

Neutralization Assay

A focus reduction microneutralization (FRµNT) technique was utilized as previously described (Crill et al., *PLoS ONE* 4(4):e991, 2009) with few modifications. Sera from vaccinated mice were diluted 1:10, heat inactivated, titrated 2-fold to the volume of 40 µL, and 320 virus FFU/40 µL were added to each dilution. FRµNT titers were calculated for each virus relative to a back titration. Exact FRµNT titers were modeled by the sigmoidal dose response with variable slope using Graph Pad Prism version 4. Values are the average of two independent replicates.

Statistical Analysis

All graphed original values are means+/−s.e.m. Data were natural-log transformed to achieve homogenous variances (Leven's test) and normality (Kolmogrovo-Smirnov test). Transformed data was analyzed with a Student's t-test with Satterthwaite correction when necessary, or ANOVA and Tukey's post-test as indicated. Statistical analysis performed with SAS 9.2. $p<0.05$ were considered significant.

Example 2

A West Nile Virus CD4 T Cell Epitope Improves the Immunogenicity of Dengue Virus Serotype 2 Vaccines This example describes the identification of a CD4 T cell epitope in the WNV E protein that significantly increases the immunogenicity of both WT and cross-reactivity reduced DENV-2 DNA vaccines.

pVWNi Vaccination Elicits Rapid Protection from Virus Challenge

Previous studies have shown three weeks post vaccination with pVWNi, mice elicited high levels of WNV neutralizing antibodies which protected 100% of mice (Davis et al., *J Virol* 75(9): 4040-4047, 2001). In order to describe the temporal kinetics of the immune response to pVWNi plasmid, C57BL/6J mice were vaccinated with a single injection of 100 µg and challenged with WNV at 1, 2, 4, 7, 14, or 21 days post vaccination and compared to 1 day and 21 days naïve age matched controls. By 4 days post vaccination, 50% PRNT titers of pooled sera was 1:128 and 100% of mice were protected from lethal challenge ($p<0.0001$) (FIG. 1), with the exception of the 7 days post challenge group ($p=0.0004$) where 2 mice succumbed to lethal disease which may also account for the lower $PRNT_{50}$ titer for the group. These data suggest the pVWNi vaccine induces a rapid, protective immune response.

Vaccination Induces a Rapid Cellular Influx and Activation

Figure 2:
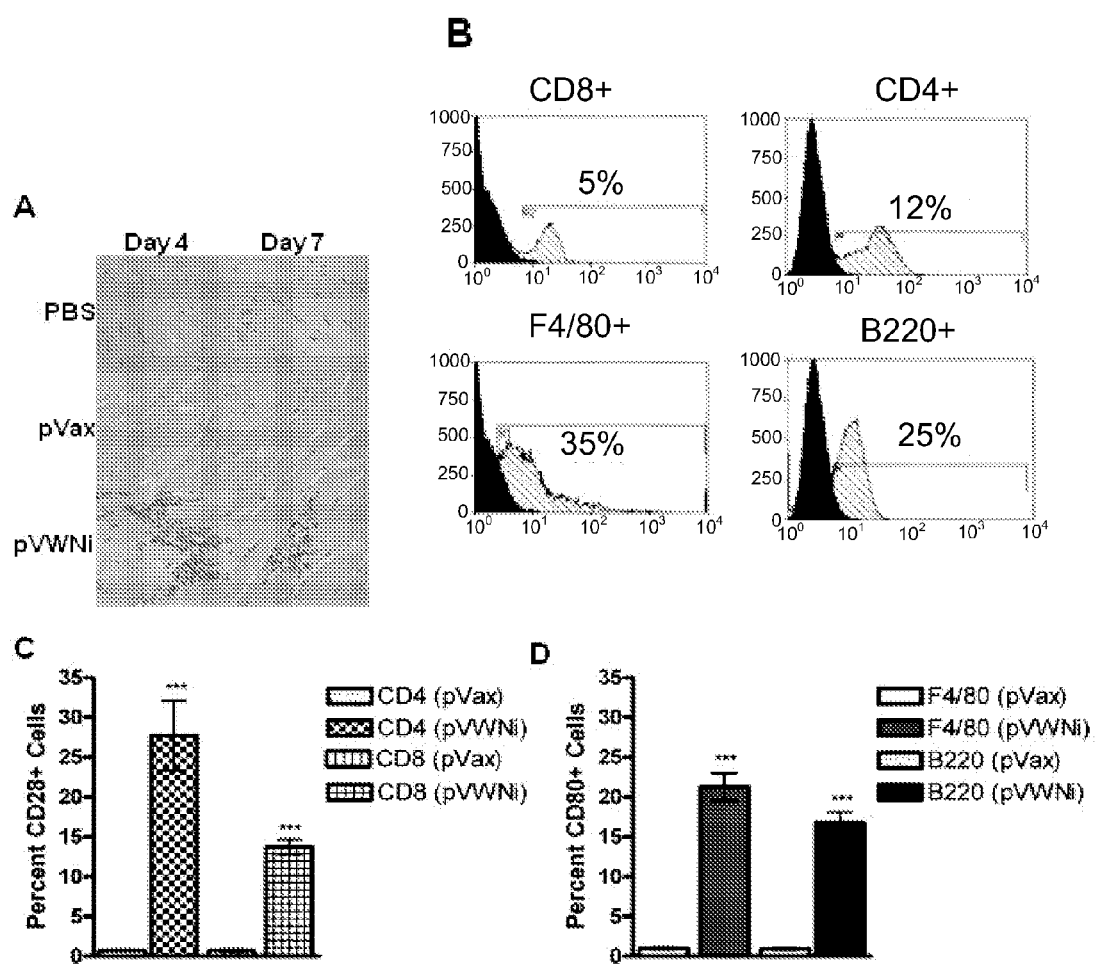
FIGS. 2A-2D show pVWNi elicits rapid cellular influx to the injection site and antigen specific activation. (A) H&E staining of cellular infiltration of dissected muscles from the injection site 4 and 7 days post vaccination with pVWNi, PBS or pVax (controls) at 600× magnification. H&E is representative of n=5. Muscles were prepared in single cell suspensions and labeled with antibodies against extracellular markers. The small lymphocyte or CD3 population was gated for analysis. Percent positive is based on $10^6$ total cells. (B) Phenotypic analysis of cells recruited to the injection site 4 days post vaccination. Histogram is representative of n=5. (C) Analysis of activated (CD28+) CD4+ or CD8+ T cells at injection site 4 days post vaccination. (D) Analysis of activated (CD80+) antigen presenting cells (F4/80+) or B cells (B220+) at injection site 4 days post vaccination. Data are expressed as mean+/−s.e.m. for n=5. Student's Test with Satterthwaite correction was used for analysis. $p<0.05$ were considered significant; triple asterisk $p<0.001$.

To understand the nature of the rapid immune response and protection elicited by pVWNi vaccination, the participation of cellular immunity in the early immune response was investigated. C57BL/6J mice were vaccinated i.m. with pVWNi, pVax (vector) and PBS as controls. Five mice per group were sacrificed at 2, 4, 7 and 14 days post vaccination for histology and flow cytometry. Muscle from the vaccination site 4 and 7 days post vaccination was dissected and histology was performed (FIG. 2A). Hematoxylin and Eosin staining revealed 4 days post vaccination with pVWNi a marked infiltration of cells with lymphocytic and monocytic morphology at the vaccination site; 7 days post vaccination the infiltrate had mostly subsided. Mock vaccination with PBS or pVax did not induce any cellular infiltrate, suggesting pVWNi induces a transgene driven, transient cellular infiltration to the injection site. Flow cytometric analysis of muscle tissue demonstrated a large proportion of the cellular infiltrate 4 days post vaccination was composed of F4/80+ antigen presenting cells and CD4+ T cells (FIG. 2B). Antigen driven CD4+ T cells accounted for significantly higher proportions of cellular infiltrates to the injection site than CD8+ T cells ($p=0.0001$). Moreover, there was a large proportion of activated T cells (FIG. 2C) and antigen presenting cells (FIG. 2D) compared to the pVax vaccinated control animals ($p<0.0001$), suggesting the cellular activation is gene specific.

Figure 8:
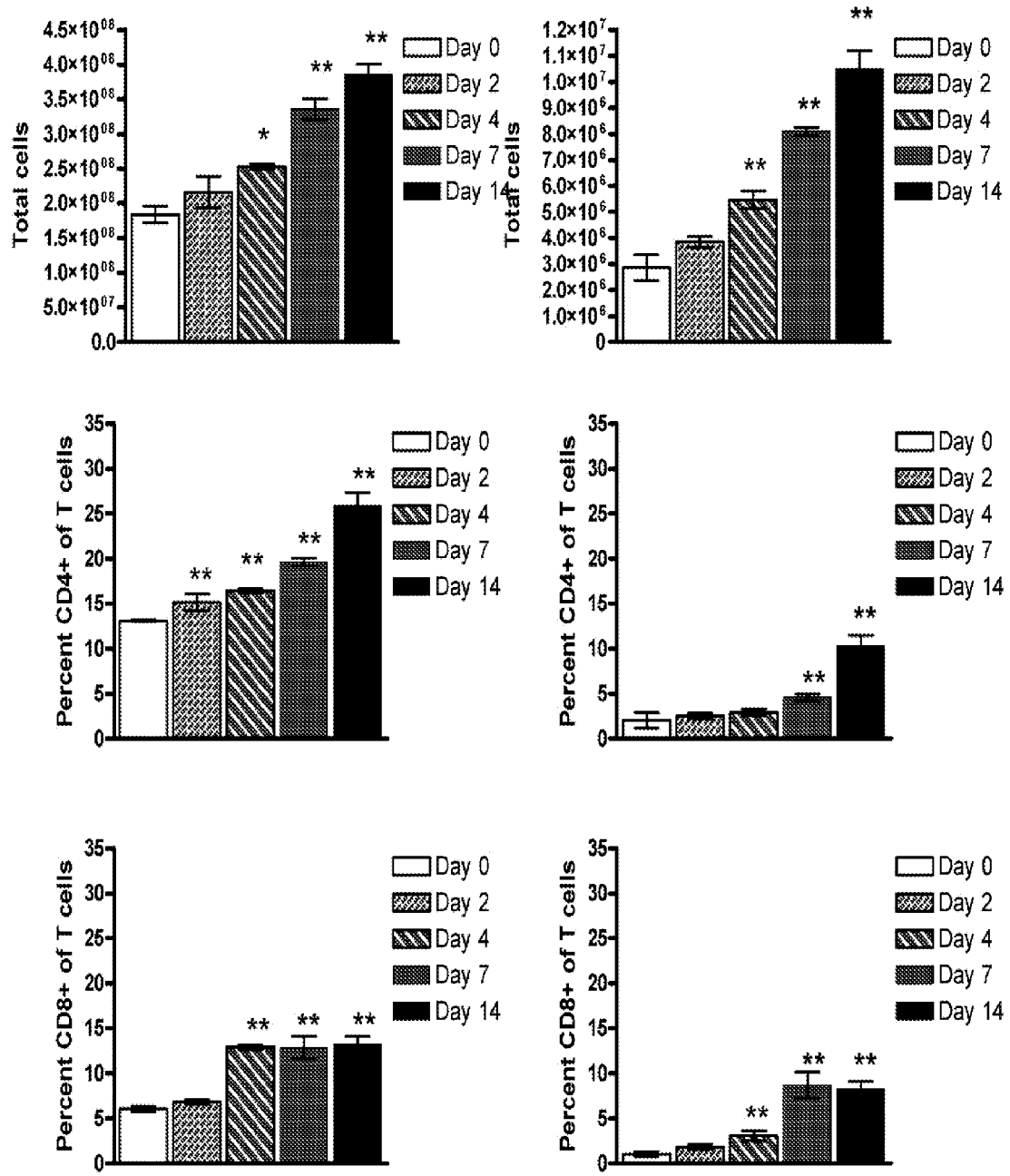
FIG. 8 is a series of bar graphs showing pVWNi vaccination increases the proportion of cellular immune cells in spleen and lymph nodes. Shown are the results of FACS analysis of T cells in spleen and lymph nodes following vaccination with pVax or pVWNi. Mice were vaccinated with either pVax or pVWNi and splenocytes harvested on day 2, 4, 7, and 14 post vaccination. Cells were labeled and gated on the CD3 and CD4 or CD8 and $10^6$ total cells were collected. All data are expressed as mean+/−s.e.m. and representative of 3 experiments with n=5. ANOVA was performed followed by a Dunnet's multiple comparison test. p values<0.05 are considered significant; single asterisk, $p<0.05$, double asterisk $p<0.01$.
Figure 9:
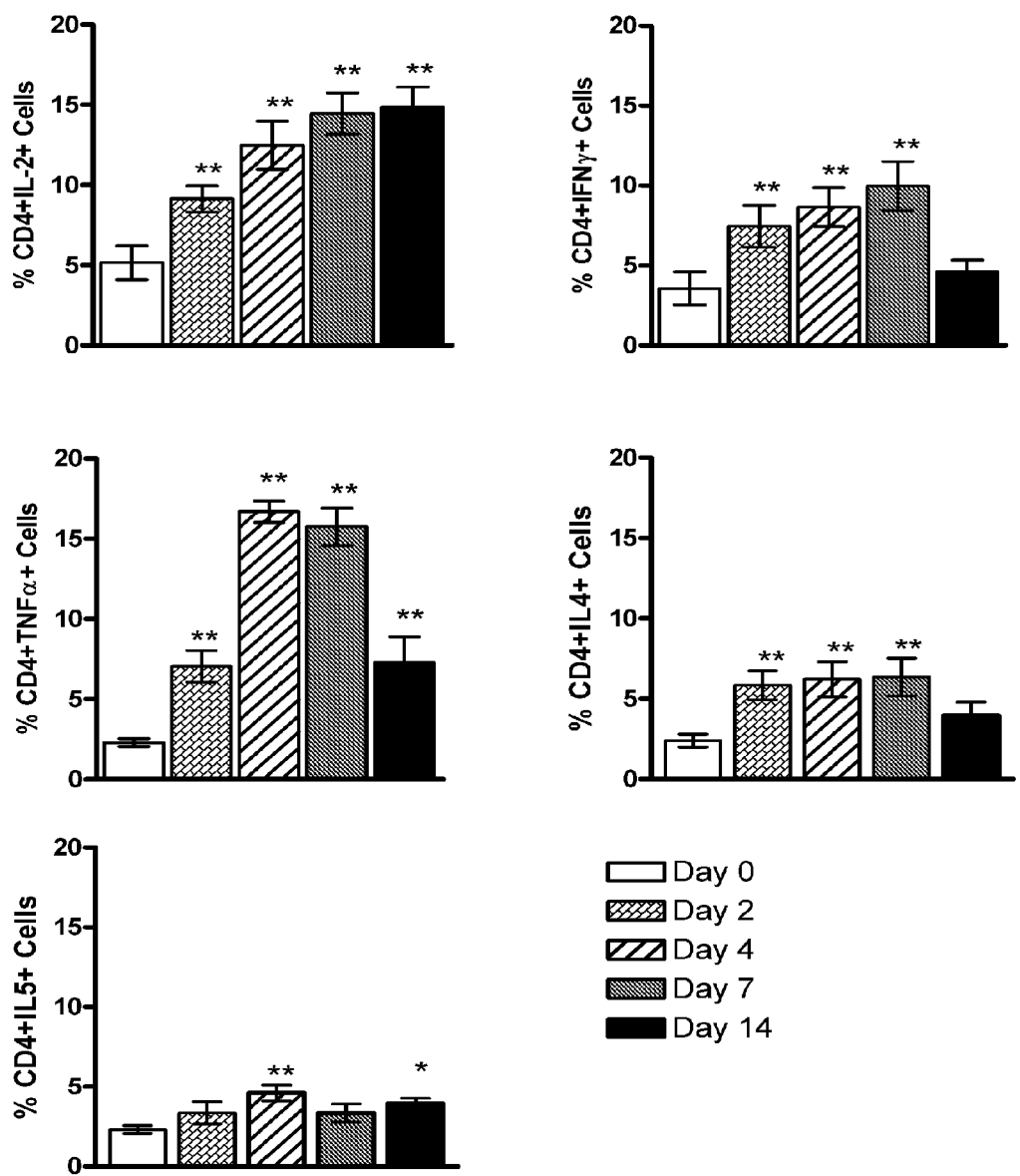
FIG. 9 is a series of bar graphs showing pVWNi vaccination elicits an antigen specific Th1 predominant CD4 T helper response. Splenocytes of vaccinated mice were harvested 0, 2, 4, 7, or 14 days post vaccination and stimulated in a mixed leukocyte reaction. CD3+/CD4+ T cells were gated, $10^6$ total cells were collected and analyzed for the presence of Th1 (IL-2, IFNγ, or TNFα) or Th2 (IL-4 or IL-5) cytokines. Data are expressed as mean+/−s.e.m. for n=5 and analyzed with ANOVA and Dunnet's multiple comparison test. $p<0.05$ were considered significant: single asterisk, $p<0.05$, double asterisk $p<0.01$.

Increases in activated T cells in the peripheral lymphatic organs could be observed as early as 2 days post vaccination in the spleen and 4 days post vaccination in the draining lymph nodes and remained through day 14, which is also evident by increased overall total cells in these organs by 4 days post vaccination (see FIG. 8). Cytokine secretion of activated CD4+ T cells indicated Th1 and Th2 cytokine production as early as 2 days post vaccination for IL-2, IFNγ, TNFα, and IL-4, and at 4 days for IL-5 (see FIG. 9). IL-2 and TNFα remained elevated through the entirety of the experiment while IFNγ and IL-4 subsided by 14 days post vaccination. These data indicate pVWNi vaccination induces both Th1 and Th2 cytokine profiles, though Th1 CD4+ T cells are predominantly elicited. Taken together, these data indicate the important role of activated Th1 CD4+ T cells and F4/80 positive antigen presenting cells in the establishment of the immune response to vaccination.

CD4 Positive Epitope Present in Transmembrane Domain of WNV

The striking rapid immune response and protection elicited by the pVWNi vaccine above prompted a comparison to the previously described DENV-2 DNA vaccine, expressing prM and 80% E (ectodomain) DENV-2 and 20% E (stem-anchor region) of Japanese encephalitis virus (JEV), which enhances the secretion of virus like particles. Unlike the pVWNi plasmid, two vaccinations of 100 µg of DENV-2 plasmid were required to elicit sufficient neutralizing antibody to passively protect neonatal mice from DENV-2 challenge (Chang et al., *Virology* 306(1):170-180, 2003). Both of these DNA vaccines contain identical transcriptional enhancer and promoter, translational control element and JEV signal sequence (Chang et al., *J Virol* 74(9):4244-4252, 2000); however, the difference in immunogenicity of the two vaccines is quite striking. The above observations led to the hypothesis that there were differential antigenic determinants between the WNV and DENV-2 DNA vaccines (pVD2i) that involved the cellular mediated arm of the immune system potentially CD4 T cell driven.

Figure 3:
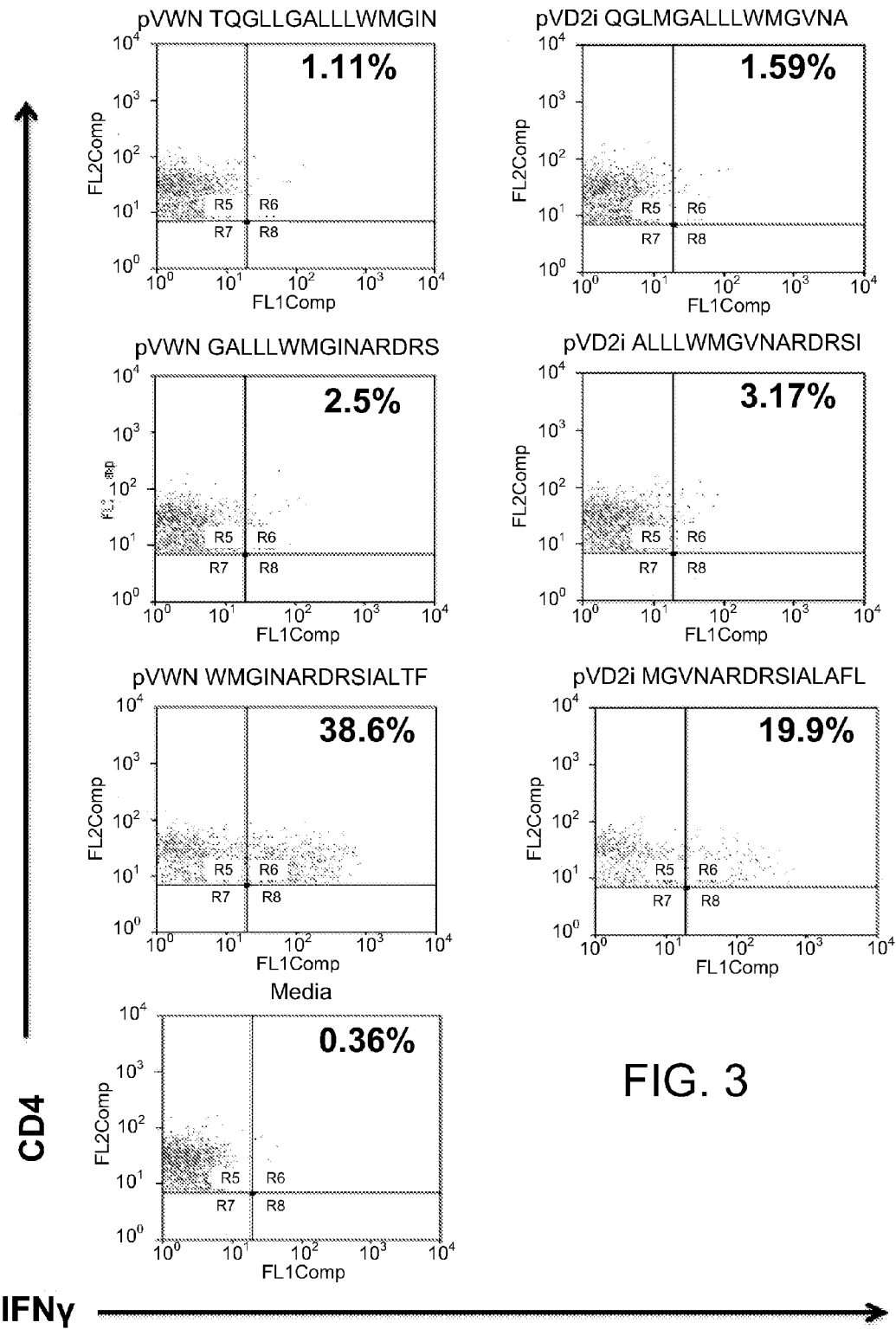
FIG. 3 is a series of dot plots demonstrating that the WNV transmembrane domain region contains a strong CD4 epitope not present in JEV. Splenocytes from mice vaccinated with pVWNi or pVD2i (containing C terminal 20% JEV E (Chang et al., *Virology* 306(1):170-180, 2003)) were stimulated ex vivo with 2 μg of envelope peptide (pVWN-TQGLLGALLL-WMGIN—SEQ ID NO: 32; pVD2i-QGLMGALLLW-MGVNA—SEQ ID NO: 33; pVWN-GALLLWMGI-NARDRS—SEQ ID NO: 34; pVD2i-ALLLWMGVNARDRSI—SEQ ID NO: 35; pVWN-WMGINARDRSIALTF—SEQ ID NO: 36; or pVD2i-MGVNARDRSIALAFL—SEQ ID NO: 37). Cells were stained for CD3, CD4 and IFNγ and 10,000 of the CD3/CD4 gated population was counted. While both pVWN-WMGI-NARDRSIALTF (SEQ ID NO: 36) and pVD2i-MGVNARDRSIALAFL (SEQ ID NO: 37) elicited IFNγ producing CD4 T cells, the response to pVWN was greater than that of pVD2i. Dot plots are representative of a single experiment (n=2).

To characterize the cellular immune response to pVWNi, an overlapping peptide library that covered the entire prM and E protein coding sequences of pVWNi and pVD2i was developed to determine differential immune responses to the two vaccine constructs. The library was initially screened using 23 peptide pools of ten 15mer peptides. C57BL/6J mice immunized with pVWNi or pVD2i were boosted at three weeks and sacrificed at 6 weeks. Spleens were homogenized and the cells used in a mixed leukocyte reaction (MLR) to determine the positive peptide pools by FACS analysis. From positive peptide pools, individual peptides were examined for further analysis. Splenocytes from vaccinated mice were incubated with 2 μg of each individual peptide and stained for CD4 or CD8 and IFNγ to identify positive reactions. A strong CD4+ epitopic region was identified in WNV E at amino acids 466-495 which was present, but much weaker in 20% JEV E (FIG. 3). This CD4 epitope of WNV E is located in two transmembrane domain (TMD) alpha helices. This is the first description of a T cell epitope present in this region of any flavivirus E protein.

Figure 4:
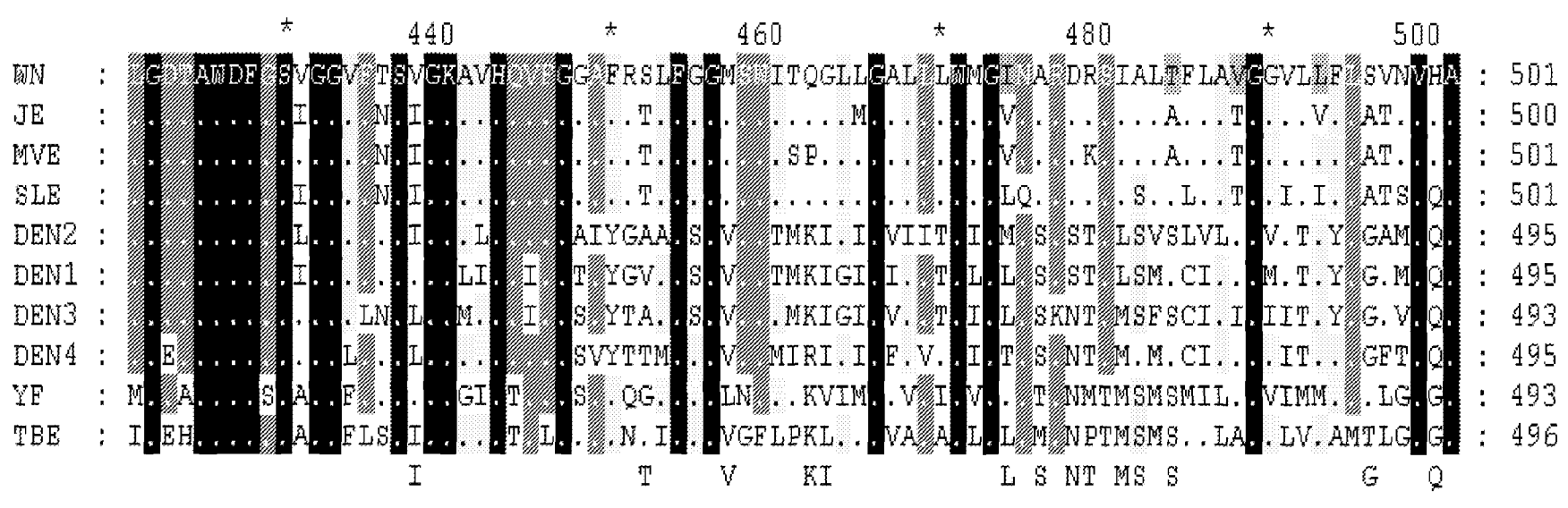

When comparing the transmembrane domain of WNV E and JEV E proteins, amino acid alignment revealed that the transmembrane domain from amino acids 466-495 are entirely conserved between WNV and JEV with the exception of four amino acids at 474, 484, 488, and 493 (FIG. 4). Using ProPed I to predict CD8 epitopes and ProPed to predict CD4 epitopes, in silico analysis revealed the transmembrane region of WNV contains promiscuous CD8 and CD4 epitopes with potential to bind to several human HLA alleles (see Table 1 below) suggesting the incorporation of this epitope may increase the immunogenicity of DENV-2 DNA vaccination in an outbred population.

TABLE 1

WNV TMD CD4 epitope may bind to several human HLA alleles

| Restriction | Allele | WNV TMD Positive Peptide Sequences*† |
|---|---|---|
| CD4 | DRB1_0101 | GALLLWMGINARDRSIALTFLAVGGVLLFLSVNVHA |
|  | DRB1_0102 | GALLLWMGINARDRSIALTFLAVGGVLLFLSVNVHA |
|  | DRB1_0306 | GALLLWMGINARDRSIALTFLAVGGVLLFLSVNVHA |
|  | DRB1_0307 | GALLLWMGINARDRSIALTFLAVGGVLLFLSVNVHA |
|  | DRB1_0308 | GALLLWMGINARDRSIALTFLAVGGVLLFLSVNVHA |
|  | DRB1_0311 | GALLLWMGINARDRSIALTFLAVGGVLLFLSVNVHA |
|  | DRB1_0401 | GALLLWMGINARDRSIALTFLAVGGVLLFLSVNVHA |
|  | DRB1_0404 | GALLLWMGINARDRSIALTFLAVGGVLLFLSVNVHA |
|  | DRB1_0405 | GALLLWMGINARDRSIALTFLAVGGVLLFLSVNVHA |
|  | DRB1_0408 | GALLLWMGINARDRSIALTFLAVGGVLLFLSVNVHA |
|  | DRB1_0410 | GALLLWMGINARDRSIALTFLAVGGVLLFLSVNVHA |
|  | DRB1_0423 | GALLLWMGINARDRSIALTFLAVGGVLLFLSVNVHA |
|  | DRB1_0426 | GALLLWMGINARDRSIALTFLAVGGVLLFLSVNVHA |
|  | DRB1_0701 | GALLLWMGINARDRSIALTFLAVGGVLLFLSVNVHA |
|  | DRB1_0703 | GALLLWMGINARDRSIALTFLAVGGVLLFLSVNVHA |
|  | DRB1_0804 | GALLLWMGINARDRSIALTFLAVGGVLLFLSVNVHA |
|  | DRB1_0806 | GALLLWMGINARDRSIALTFLAVGGVLLFLSVNVHA |
|  | DRB1_0813 | GALLLWMGINARDRSIALTFLAVGGVLLFLSVNVHA |
|  | DRB1_1102 | GALLLWMGINARDRSIALTFLAVGGVLLFLSVNVHA |
|  | DRB1_1107 | GALLLWMGINARDRSIALTFLAVGGVLLFLSVNVHA |
|  | DRB1_1114 | GALLLWMGINARDRSIALTFLAVGGVLLFLSVNVHA |
|  | DRB1_1121 | GALLLWMGINARDRSIALTFLAVGGVLLFLSVNVHA |
|  | DRB1_1304 | GALLLWMGINARDRSIALTFLAVGGVLLFLSVNVHA |
|  | DRB1_1307 | GALLLWMGINARDRSIALTFLAVGGVLLFLSVNVHA |
|  | DRB1_1321 | GALLLWMGINARDRSIALTFLAVGGVLLFLSVNVHA |
|  | DRB1_1322 | GALLLWMGINARDRSIALTFLAVGGVLLFLSVNVHA |
|  | DRB1_1323 | GALLLWMGINARDRSIALTFLAVGGVLLFLSVNVHA |
|  | DRB1_1501 | GALLLWMGINARDRSIALTFLAVGGVLLFLSVNVHA |
|  | DRB1_1502 | GALLLWMGINARDRSIALTFLAVGGVLLFLSVNVHA |
|  | DRB1_1506 | GALLLWMGINARDRSIALTFLAVGGVLLFLSVNVHA |
|  | DRB5_0101 | GALLLWMGINARDRSIALTFLAVGGVLLFLSVNVHA |
|  | DRB5_0105 | GALLLWMGINARDRSIALTFLAVGGVLLFLSVNVHA |
| CD8 | HLA-A*0201 | GALLLWMGINARDRSIALTFLAVGGVLLFLSVNVHA |
|  | HLA-A*0205 | GALLLWMGINARDRSIALTFAVGGVLLFLSVNVHA |
|  | HLA-A24 | GALLLWMGINARDRSIALTFLAVGGVLLFLSVNVHA |
|  | HLA-A3 | GALLLWMGINARDRSIALTFLAVGGVLLFLSVNVHA |
|  | HLA-A*3101 | GALLLWMGINARDRSIALTFLAVGGVLLFLSVNVHA |
|  | HLA-A*3302 | GALLLWMGINARDRSIALTFLAVGGVLLFLSVNVHA |
|  | HLA-A2.1 | GALLLWMGINARDRSIALTFLAVGGVLLFLSVNVHA |
|  | HLA-B14 | GALLLWMGINARDRSIALTFLAVGGVLLFLSVNVHA |
|  | HLA-B*2702 | GALLLWMGINARDRSIALTFLAVGGVLLFLSVNVHA |
|  | HLA-B*2705 | GALLLWMGINARDRSIALTFLAVGGVLLFLSVNVHA |
|  | HLA-B*3501 | GALLLWMGINARDRSIALTFLAVGGVLLFLSVNVHA |
|  | HLA-B*3701 | GALLLWMGINARDRSIALTFLAVGGVLLFLSVNVHA |
|  | HLA-B*3901 | GALLLWMGINARDRSIALTFLAVGGVLLFLSVNVHA |
|  | HLA-B*5101 | GALLLWMGINARDRSIALTFLAVGGVLLFLSVNVHA |
|  | HLA-B*5102 | GALLLWMGINARDRSIALTFLAVGGVLLFLSVNVHA |
|  | HLA-B*5103 | GALLLWMGINARDRSIALTFLAVGGVLLFLSVNVHA |
|  | HLA-B*5401 | GALLLWMGINARDRSIALTFLAVGGVLLFLSVNVHA |
|  | HLA-B*51 | GALLLWMGINARDRSIALTFLAVGGVLLFLSVNVHA |
|  | HLA-B*5801 | GALLLWMGINARDRSIALTFLAVGGVLLFLSVNVHA |
|  | HLA-B7 | GALLLWMGINARDRSIALTFLAVGGVLLFLSVNVHA |
|  | HLA-B*0702 | GALLLWMGINARDRSIALTFLAVGGVLLFLSVNVHA |
|  | HLA-B8 | GALLLWMGINARDRSIALTFLAVGGVLLFLSVNVHA |

†WNV TMD sequence shown includes E amino acids 466-501 (SEQ ID NO: 6)
*Positive ProPed nanomers are in bold and obligatory P1 binding residues are underlined Incorporation of WNV CD4 Epitope to pVD2i Increases Vaccine Immunogenicity The identification of a strong CD4 epitope in the WNV TMD and its ability to potentially be a promiscuous CD4 and CD8 epitope led to an investigate to determine if this epitope could increase the immunogenicity of the DENV-2 DNA vaccine, pVD2i. Using site-directed mutagenesis, the four amino acids at the C-terminal 20% JEV E in pVD2i were sequentially changed to the corresponding amino acids in pVWNi. These changes produced the plasmids designated pVD21V474I (pVD2i-I), pVD21V474I/A484T (pVD2i-IT), pVD21V474I/A484T/T488V (pVD2i-ITV), and pVD21V474I/A484T/T488V/V493L (pVD2i-ITVL).

Figure 10:
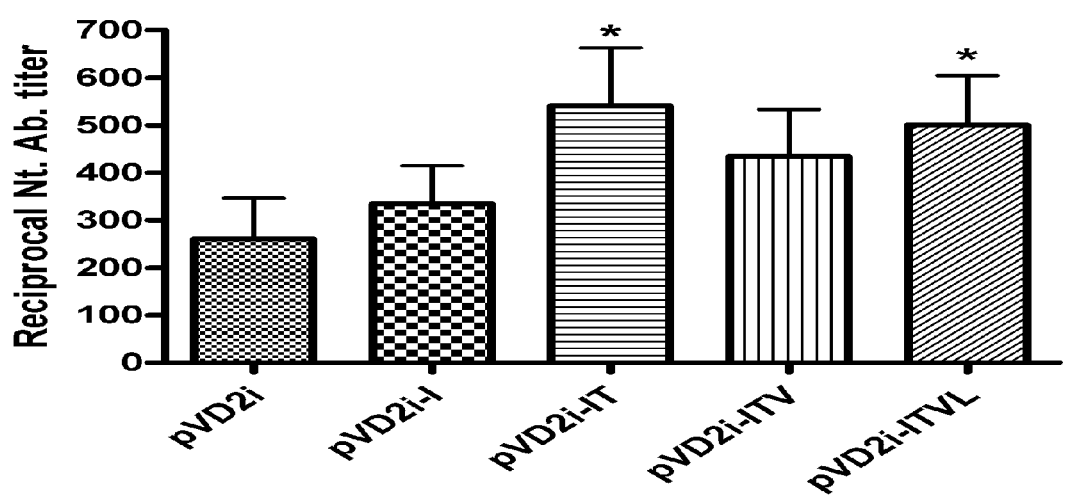
FIG. 10 is a bar graph showing incorporation of WNV TMD CD4 epitope amino acids increases neutralizing antibody titers after the second substitution. FRμNT$_{50}$ DENV-2 neutralizing antibody (Nt. Ab.) titers of C57BL/6 mice vaccinated with pVD2i with sequential addition of the WNV TMD amino acids. Data are expressed as mean+/−s.e.m. for n=5. ANOVA and Tukey's post test was performed on transformed data, $p<0.05$ were considered significant: single asterisk, $p<0.05$.

To first investigate differences in immunogenicity of the WNV CD4 TMD epitope, C57BL/6J mice were immunized with each construct, boosted on week-4 and sacrificed on week-8. To assess immunogenicity between the constructs, focus reduction microneutralization (FRµNT) was performed on individual mouse sera. Eight weeks post vaccination, pVD2i-I, the first amino acid, did not increase the neutralizing antibody titer compared to pVD2i (p=0.20) (see FIG. 10). However, vaccines containing the second, third, and fourth amino acid changes appeared to elicit increased levels of neutralizing antibody with pVD2i-IT (p=0.02), and pVD2i-ITVL (p=0.04) being significant. This suggests amino acid 474, located in the first transmembrane helix, may not be an integral part of the CD4 epitope as the subsequent amino acid substitutions at WNV E positions 484, 488, and 493, located in the second transmembrane helix, elicited higher levels of neutralizing antibodies compared to pVD2i. Also supporting this is the presence of a trypsin cleavage site located between the first and second transmembrane helices which could cleave the transmembrane region into two separate peptides.

Cross-reactivity reduced DENV-2 DNA vaccines that limit the production of cross-reactive antibodies and vaccine induced antibody-dependent enhancement of infection have been produced. Cross-reactivity reduced DENV-2 DNA vaccines were designed by introducing specific substitutions into the E fusion peptide (at G106 and L107) and into serocomplex cross-reactive epitopes of E domain III (at K310, E311 and P364), to generate vaccine candidates that dampen or eliminate the induction of cross-reactive, enhancing antibodies recognizing weakly or non-neutralizing epitopes. These novel vaccines, however, exhibited a trend to reduce neutralizing antibody titer when compared to the wild type pVD2i vaccine (WT). To determine if the incorporation of the WNV TMD CD4 epitope could increase the immunogenicity of the DENV-2 cross-reactivity reduced vaccine, the WNV CD4 epitope V474I/A484T/T488V/V493L (TMD) was introduced into the cross-reactivity reduced DENV-2 DNA vaccine pVD21G106R/L107D/K310E/E311R/P364R (RDERR) to create pVD21G106R/L107D/K310E/E311R/P364R/V474I/A484T/T488V/V493L (RDERR-TMD) and the immunogenicity of pVD2i (WT), pVD21V474I/A484T/T488V/V493L (WT-TMD), RDERR, and RDERR-TMD were compared by FRµNT. Swiss Webster mice were immunized, boosted at 4 weeks, and sacrificed at 12 weeks.

Figure 5:
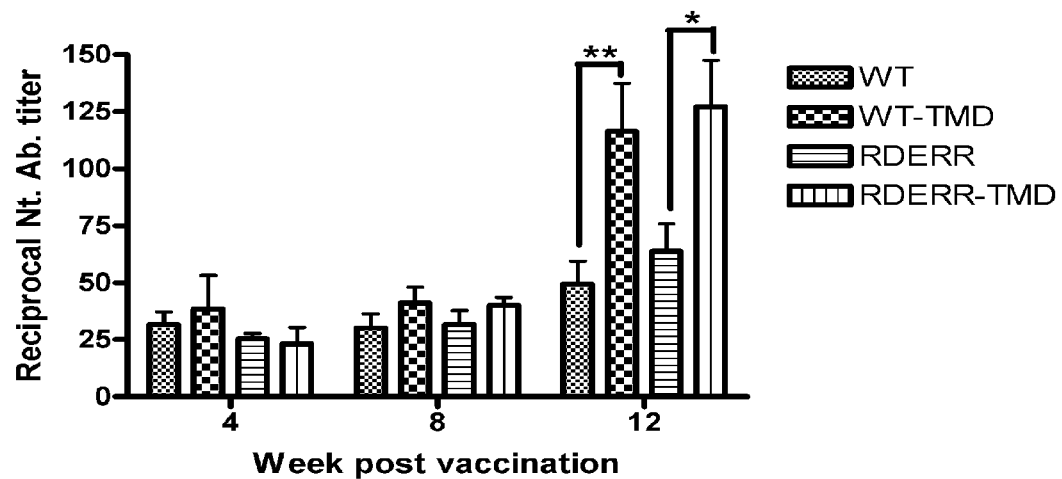
FIG. 5 is a bar graph showing the incorporation of the WNV TMD CD4 epitope increases the immunogenicity of DENV-2 DNA vaccines. FRμNT$_{50}$ DENV-2 neutralizing antibody (Nt. Ab.) titers of Swiss Webster mice 4, 8, and 12 weeks post vaccination. Data are expressed as mean+/−s.e.m. for n=10. Student's Test with Satterthwaite correction was used to compare vaccine treatments as indicated. $p<0.05$ were considered significant: single asterisk, $p<0.05$, double asterisk $p<0.01$.

DENV-2 neutralizing antibody titers between the vaccines at 4 and 8 weeks post vaccination did not differ (FIG. 5), however, 8 weeks post vaccination we observed a trend for increased neutralization in TMD containing vaccines. Although previous observations suggested Swiss Webster mice to be less immunogenic than C57BL/6 to this system, twelve weeks post vaccination WT-TMD (p=0.008) and RDERR-TMD (p=0.02) elicited significantly more DENV-2 neutralizing antibodies compared to WT and RDERR, respectively. Moreover, incorporation of the WNV TMD CD4 epitope did not elicit a significant difference in neutralizing antibody titers between WT-TMD and RDERR-TMD (p=0.71). This suggested that addition of the WNV TMD CD4 epitope significantly increases the immunogenicity of both WT and cross-reactivity reduced DENV-2 DNA vaccines.

WNV CD4 Epitope Upregulates CD154 on CD4 T Cells

Cell to cell interactions play a pivotal role in regulating the immune response. CD154 is expressed on a variety of cells, including but not limited to, activated CD4 T cells, CD8 T cells, mast cells, basophils, and eosinophils (Grewal and Flavell, *Annu Rev Immunol* 16: 111-135, 1998). CD154 is the ligand for CD40, which is expressed on B cells, antigen presenting cells, epithelium cells and endothelial cells among others. The ligation of CD154 and CD40 results in T cell activation, B cell activation, and APC activation and extravasation. Blocking the CD154 and CD40 interaction reveals a primary role of CD154 in regulating B cell proliferation, production of immunoglobulins (Ig), Ig class switching, germinal center formation, and generation of memory B cells (Clark et al., *Adv Immunol* 63: 43-78, 1996).

Figure 6:
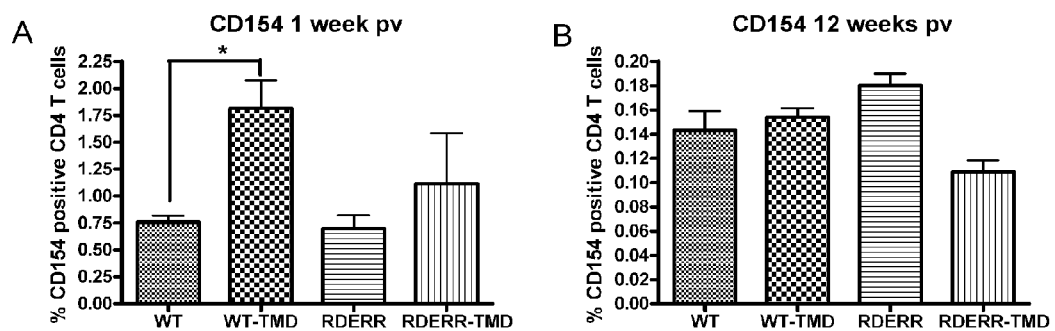
FIGS. 6A and 6B are bar graphs showing WNV TMD CD4 epitope induces early CD154 expression on CD4 T cells. Splenocytes from vaccinated mice were stimulated ex vivo with UV inactivated DENV-2. The CD3+/CD4+ T cell population was gated and 40,000 gated events were analyzed. (A) CD154 expression of Swiss Webster CD4 T cells one week post vaccination (pv). (B) CD154 expression of Swiss Webster CD4 T cells 12 weeks post vaccination. Data are expressed as mean+/−s.e.m. for n=5. Student's Test with Satterthwaite correction was used to compare vaccine treatments as indicated or ANOVA with Tukey's post test was performed on transformed data. $p<0.05$ were considered significant: single asterisk, $p<0.05$.
Figure 11:
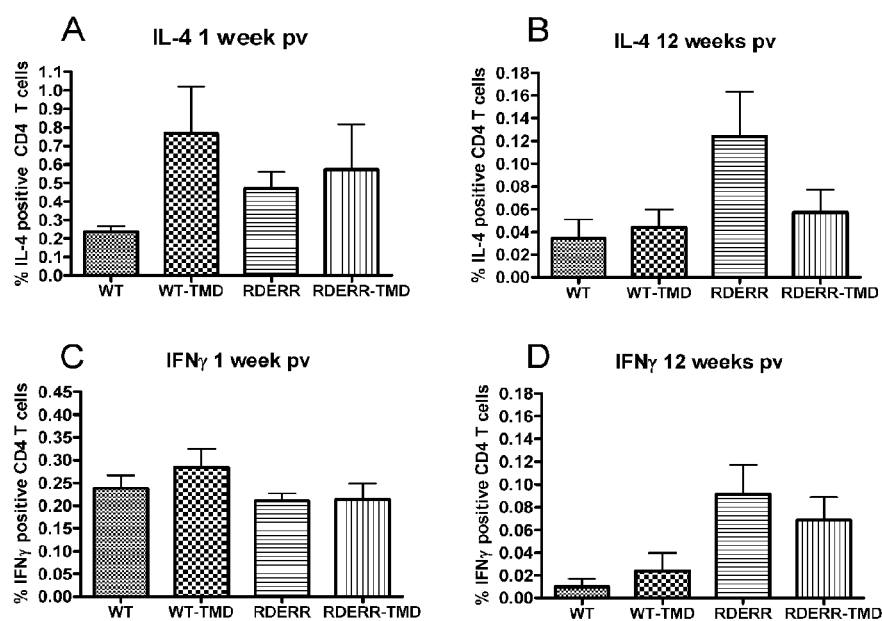
FIGS. 11A-11D are bar graphs showing vaccination with DENV-2 DNA vaccines induces a predominant early Th2 driven CD4 T cell response. Splenocytes from vaccinated mice were stimulated ex vivo with UV inactivated DENV-2. The CD3+/CD4+ T cell population was gated and 40,000 gated events were analyzed. Th2 driven T cell responses of Swiss Webster mice one (A) and (B) 12 weeks pv. *Th*1 driven T cell responses of Swiss Webster mice one (C) and (D) 12 weeks pv. Data are expressed as mean+/−s.e.m. for n=5 (1 week pv) or n=10 (12 weeks pv). Student's Test with Satterthwaite correction was used to compare vaccine treatments as indicated. $p<0.05$ were considered significant.

To better understand the mechanism of the observed antibody increases, the potential of the WNV TMD CD4 epitope to increase the expression of CD154 on CD4 T cells was investigated. Swiss Webster mice were vaccinated with 100 µg of WT, WT-TMD, RDERR or RDERR-TMD on weeks 0 and 4. Five mice per group were sacrificed one week post vaccination, and the remaining 10 mice per group were sacrificed 12 weeks post vaccination. Freshly harvested spleens were homogenized and stimulated in a MLR. One week post vaccination, WT-TMD vaccinated splenocytes elicited significantly higher levels of CD154 expressing T cells (p=0.013) compared to WT vaccinated splenocytes, while RDERR-TMD vaccinated splenocytes exhibited the same trend for increased CD154 expression (FIG. 6). These data suggest the WNV TMD CD4 epitope may act early in the immune response to up regulate CD154 on CD4 T cells, potentially increasing the neutralizing antibody titers. In addition, stimulated splenocytes 1 week post vaccination elicited a higher percentage of IL-4 positive CD4 T cells than IFNγ positive CD4 T cells, suggesting the predominance of a Th2 driven T cell response (see FIG. 11).

Twelve weeks post vaccination, all stimulated splenocytes continued to elicit both Th1 and Th 2 driven T cell responses, though their magnitudes were greatly reduced compared to 1 week post vaccination. Additionally, 12 weeks post vaccination there were no differences in CD154 expression on CD4 T cells between WT and WT-TMD or RDERR and RDERR-TMD (see FIG. 11). This observation and the greatly reduced magnitudes of all of these responses 12 weeks post vaccination together suggest WNV TMD CD4 epitope induces early CD154 expression as a potential mechanistic basis for the increased immunogenicity of this vaccine modification.

WNV CD4 Epitope Increases Immunogenicity of DENV VLP Vaccine

Figure 7:
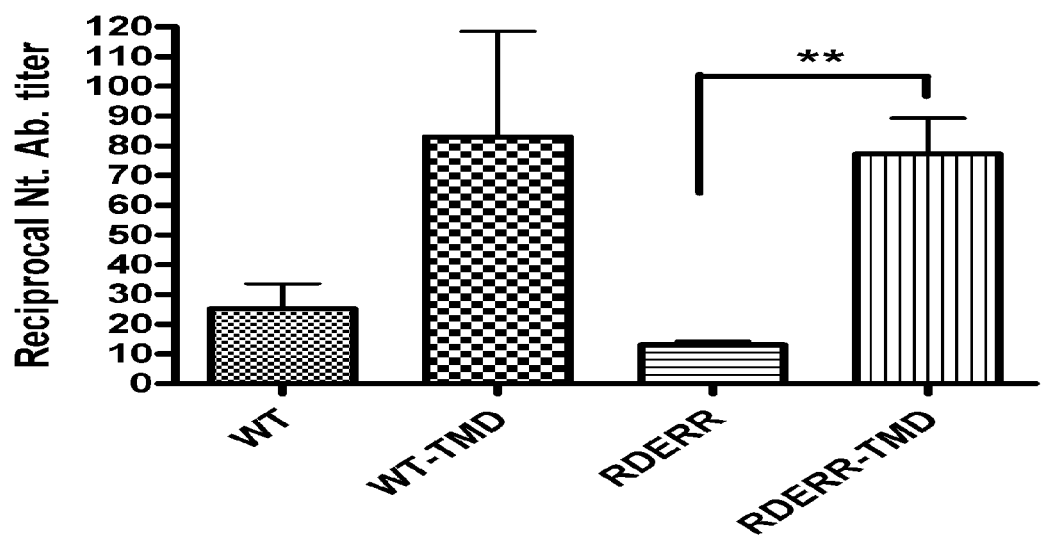
FIG. 7 is a bar graph demonstrating that the WNV TMD CD4 epitope increases immunogenicity of DENV-2 VLP vaccines. FRμNT$_{50}$ DENV-2 Nt. Ab. titers of Swiss Webster mice vaccinated with 1 μg of VLP. Data are expressed as mean+/−s.e.m. for n=5. Student's t test with Satterthwaite correction was used to compare vaccine treatments as indicated, $p<0.05$ were considered significant: double asterisk, $p<0.01$.

Immunogenic proteins encoding neutralizing epitopes are a commonly used platform to stimulate protective immunity against many pathogens. To investigate the benefit of adding the WNV CD4 epitope to alternative vaccine formats, Swiss Webster mice were immunized with 1 µg of purified WT, WT-TMD, RDERR, or RDERR-TMD VLPs. All vaccines were formulated with 8% Alum, boosted at 4 weeks and sacrificed at 8 weeks. The neutralizing antibody titer of WT-TMD VLP (p=0.055) and RDERR-TMD VLP (p=0.005) was increased compared to the WT VLP and RDERR VLP vaccines respectively (FIG. 7). These results were similar to those observed for the DENV-2 DNA vaccines (FIG. 5) and suggest incorporation of the WNV TMD CD4 epitope can increase vaccine immunogenicity for other vaccine formats and is not solely functional in DNA vaccine formats.

Discussion

Increasing the immunogenicity of DNA vaccines has been an active area of investigation as some DNA vaccines are hindered by low immunogenicity and efficacy. The incorporation of the WNV TMD CD4 epitope significantly increased the immunogenicity of DENV-2 DNA vaccine (WT, pVD2i) and also the cross-reactivity reduced DENV-2 DNA vaccine, RDERR. This increased immunogenicity appears to be due in part to an early increase in activated CD154 CD4 T cells. Traditional methods to increase the immunogenicity of DNA vaccination have included the use of genetic adjuvants where immunostimulatory molecules are encoded into the DNA vaccine, such as CpG motifs, cytokines, chemokines, GM-CSF, and ubiquitin (Chiarella et al., *Recent Pat Antiinfect Drug Discov* 3(2): 93-101, 2008). Immunostimulatory epitopes have also been investigated in several vaccine fields. One such method includes the fusion of a foreign universal T cell epitope sequence to the target gene of interest. Zhu et al. fused the FrC fragment of tetanus toxin to a DNA vaccine containing the sequence for the protective epitope of PorA protein of *Neisseria meningitides* (Zhu et al., *Infect Immun* 76(1): 334-338, 2008). The incorporation of the tetanus epitope significantly increased the immunogenicity of the DNA vaccine and induced bactericidal antibodies. In a similar approach, a polyepitope DNA vaccine was constructed using the strong CD8 immunostimulatory properties of the hepatitis B small surface antigen (HBsAg) simultaneously encoding cytotoxic T lymphocyte epitopes from six different viruses (Chen et al., *Virology* 398(1): 68-78, 2010). The new plasmid using the HBsAg epitopes as an adjuvant resulted in significant development of CTL responses to all six viruses compared to the polyepitope DNA without the HBsAg. One concern with this method is the presence of HBsAg antibody present in human sera due to hepatitis B virus (HBV) vaccination potentially interfering with vaccination efficacy or unbalanced HBV immune responses.

Although DNA vaccination in clinical trials has been proven safe, concerns about tumorigenic potential due to DNA integration and the development of DNA autoimmunity remain. For this reason, protein vaccines are frequently utilized, but are similarly hindered by lower immunogenicity than their live-attenuated counterparts. VLP vaccines are an attractive alternative to conventional protein vaccines as they can induce a strong immune response without the use of adjuvants, however, they are frequently administered with adjuvant formulations. Currently, there are few adjuvants approved for clinical use (Brunner et al., *Immunol Lett* 128 (1): 29-35, 2010) leaving an inherent need for new methods to increase the immunogenicity of protein and VLP vaccines.

Similar to strategies of DNA vaccination, the use of T helper epitopes to increase the immunogenicity of protein vaccines has also been investigated utilizing a universal T cell epitope. Lu et al. (Lu et al., *Vaccine* 27(39): 5411-5418, 2009) were able to increase the anti-tumor ability of a HSP60-fused gastrin-release peptide DNA vaccine by heterologously boosting with a recombinant protein which also contained a foreign T helper epitope of HSP70.

This approach to increase the immunogenicity of the DENV-2 DNA and VLP vaccines utilizes a naturally occurring flavivirus CD4 epitope in contrast to previous studies using foreign universal T cell epitopes. There is limited concern of humoral immunity toward the WNV TMD CD4 epitope from previous exposure interfering with the vaccine efficacy. The transmembrane domain of flaviviruses is either of low B cell antigenicity or antigenically inert, as vaccination with DENV-2 DNA plasmid containing 80% DENV-2 E and the C terminal 20% JEV E did not elicit any measurable antibody response against JEV (Chang et al., *Virology* 306(1): 170-180, 2003) and no B cell epitopes have previously been identified. Utilizing this WNV TMD CD4 epitope to increase vaccine immunogenicity has additionally advantageous since the transmembrane domain does not affect the proper antigenic folding of E.

Incorporating a naturally occurring dominant CD4 epitope may offer advantages in additional flavivirus vaccination formats. The variable yet highly conserved nature of the flavivirus transmembrane domain (FIG. 4) suggests potential differential T cell antigenicity across the flaviviruses, which can be readily manipulated as demonstrated in this study. With the global resurgence and expansion of flaviviruses, there will be increasing demand and utility for multivalent flavivirus vaccines. Multivalent vaccine interference is a frequently observed phenomenon that may be caused by competition for resources in the lymph nodes, changes in the Th1/Th2/Th0 balance, induction of regulatory T cells, and replicative interference (Guy et al., *Am J Trop Med Hyg* 80(2): 302-311, 2009; Dagan et al., *Vaccine* 28(34): 5513-23, 2010). These data show the incorporation of the strong WNV CD4 epitope into DENV-2 vaccines of different immunogenicity produces similar monovalent antibody titers.

The incorporation of naturally occurring dominant CD4 epitopes in one component of a multivalent vaccine to increase vaccine immunogenicity of a weaker component may be a possible generalized strategy for multivalent vaccines hindered by imbalanced immunogenicity or interference. For example, serotype specific immune interference affecting vaccine immunogenicity of multivalent human papilloma virus (HPV) VLP vaccine was recently demonstrated (Zhang et al., *Vaccine* 28(19): 3479-87, 2010). Licensed tetravalent vaccine containing VLP for HPV serotypes 16/18/6/11 elicited a balanced serotype specific neutralizing antibody response, while the trivalent HPV 16/18/58 displayed significant decreases in type specific neutralizing antibodies to serotype 58.

In view of the many possible embodiments to which the principles of the disclosure may be applied, it should be recognized that the illustrated embodiments are only preferred examples of the disclosure and should not be taken as limiting the scope of the disclosure. Rather, the scope of the disclosure is defined by the following claims. We therefore claim all that comes within the scope and spirit of these claims.

The invention claimed is:

1. An isolated mutant flavivirus E-glycoprotein polypeptide, wherein the polypeptide comprises an isoleucine at position 474, a threonine at position 484, a valine at position 488 and a leucine at position 493, each numbered with reference to the West Nile virus E-glycoprotein polypeptide sequence of SEQ ID NO: 38, wherein the amino acid sequence of the polypeptide comprises SEQ ID NO: 12, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31.

2. The polypeptide of claim 1, wherein the flavivirus is DENV-2, DENV-1, DENV-3, DENV-4, Japanese encephalitis virus (JEV), Murray Valley encephalitis virus (MVEV), St. Louis encephalitis virus (SLEV), yellow fever virus (YFV) or tick-borne encephalitis virus (TBEV).

3. The polypeptide of claim 2, wherein the flavivirus is DENV-2.

4. An isolated virus-like particle (VLP) comprising the polypeptide of claim 1.

5. The VLP of claim 4, further comprising a prM protein.

6. A recombinant nucleic acid molecule encoding the polypeptide of claim 1.

7. The recombinant nucleic acid molecule of claim 6, comprising the nucleotide sequence of SEQ ID NO: 10.

8. A vector comprising the recombinant nucleic acid molecule of claim 6.

9. An isolated cell comprising the vector of claim 8.

10. A composition comprising the VLP of claim 4 and a pharmaceutically acceptable carrier.

11. The composition of claim 10, further comprising an adjuvant.

12. A method of eliciting an immune response in a subject against a flavivirus, comprising administering to the subject a therapeutically effective amount of the VLP of claim 4, thereby eliciting an immune response in the subject against flavivirus.

13. The method of claim 12, wherein the subject is a mammal.

14. The method of claim 12, wherein the subject is human.

* * * * *

SEQUENCE LISTING

<160> NUMBER OF SEQ ID NOS: 38

<210> SEQ ID NO 1
<211> LENGTH: 36
<212> TYPE: DNA

-continued

```
<213> ORGANISM: Artificial Sequence
<220> FEATURE:
<223> OTHER INFORMATION: synthetic polynucleotide

<400> SEQUENCE: 1
gtctcgtgcg tttatgccca tccagagcag tagggc                              36

<210> SEQ ID NO 2
<211> LENGTH: 38
<212> TYPE: DNA
<213> ORGANISM: Artificial Sequence
<220> FEATURE:
<223> OTHER INFORMATION: synthetic polynucleotide

<400> SEQUENCE: 2
cacaccccct gtggctaaga aggtcaaagc attgatcg                            38

<210> SEQ ID NO 3
<211> LENGTH: 34
<212> TYPE: DNA
<213> ORGANISM: Artificial Sequence
<220> FEATURE:
<223> OTHER INFORMATION: synthetic polynucleotide

<400> SEQUENCE: 3
gaacacgagc acacccccta cggctaagaa ggtc                                34

<210> SEQ ID NO 4
<211> LENGTH: 34
<212> TYPE: DNA
<213> ORGANISM: Artificial Sequence
<220> FEATURE:
<223> OTHER INFORMATION: synthetic polynucleotide

<400> SEQUENCE: 4
gcacattggt cgctaagaac aggagcacac cccc                                34

<210> SEQ ID NO 5
<211> LENGTH: 36
<212> TYPE: PRT
<213> ORGANISM: West Nile virus

<400> SEQUENCE: 5

Gly Ala Leu Leu Leu Trp Met Gly Ile Asn Ala Arg Asp Arg Ser Ile
1               5                   10                  15

Ala Leu Thr Phe Leu Ala Val Gly Gly Val Leu Leu Phe Leu Ser Val
            20                  25                  30

Asn Val His Ala
        35

<210> SEQ ID NO 6
<211> LENGTH: 30
<212> TYPE: PRT
<213> ORGANISM: West Nile virus

<400> SEQUENCE: 6

Gly Ala Leu Leu Leu Trp Met Gly Ile Asn Ala Arg Asp Arg Ser Ile
1               5                   10                  15

Ala Leu Thr Phe Leu Ala Val Gly Gly Val Leu Leu Phe Leu
            20                  25                  30

<210> SEQ ID NO 7
<211> LENGTH: 2191
<212> TYPE: DNA
```

```
<213> ORGANISM: Artificial Sequence
<220> FEATURE:
<223> OTHER INFORMATION: Synthetic Construct
<220> FEATURE:
<221> NAME/KEY: CDS
<222> LOCATION: (73)..(570)
<223> OTHER INFORMATION: prM coding sequence
<220> FEATURE:
<221> NAME/KEY: misc_feature
<222> LOCATION: (571)..(1755)
<223> OTHER INFORMATION: E coding sequence
<220> FEATURE:
<221> NAME/KEY: misc_feature
<222> LOCATION: (1796)..(1928)
<223> OTHER INFORMATION: intron
<220> FEATURE:
<221> NAME/KEY: misc_feature
<222> LOCATION: (1929)..(2188)
<223> OTHER INFORMATION: E coding sequence

<400> SEQUENCE: 7
```

| | |
|---|---:|
| atgggcaaga ggtccgccgg ctcaatcatg tggctcgcga gcttggcagt tgtcatagct | 60 |

| | | | | | | | | | | | | | |
|---|---|---|---|---|---|---|---|---|---|---|---|---|---:|
| tgtgcaggcg | cc ttc | cat | tta | acc | aca | cgt | aac | gga | gaa | cca | cac atg | atc | 111 |
| | Phe | His | Leu | Thr | Thr | Arg | Asn | Gly | Glu | Pro | His Met | Ile | |
| | 1 | | | 5 | | | | | 10 | | | | |
| gtc | agc | aga | caa | gag | aaa | ggg | aaa | agt | ctt | ctg | ttt aaa | aca gag gat | 159 |
| Val | Ser | Arg | Gln | Glu | Lys | Gly | Lys | Ser | Leu | Leu | Phe Lys | Thr Glu Asp | |
| 15 | | | | | 20 | | | | | 25 | | | | |
| ggc | gtg | aac | atg | tgt | acc | ctc | atg | gcc | atg | gac | ctt ggt | gaa ttg tgt | 207 |
| Gly | Val | Asn | Met | Cys | Thr | Leu | Met | Ala | Met | Asp | Leu Gly | Glu Leu Cys | |
| 30 | | | | 35 | | | | | 40 | | | | 45 | |
| gaa | gac | aca | atc | acg | tac | aag | tgt | ccc | ctt | ctc | agg cag | aat gag cca | 255 |
| Glu | Asp | Thr | Ile | Thr | Tyr | Lys | Cys | Pro | Leu | Leu | Arg Gln | Asn Glu Pro | |
| | | | | 50 | | | | | 55 | | | | 60 | |
| gaa | gac | ata | gac | tgt | tgg | tgc | aac | tct | acg | tcc | acg tgg | gta act tat | 303 |
| Glu | Asp | Ile | Asp | Cys | Trp | Cys | Asn | Ser | Thr | Ser | Thr Trp | Val Thr Tyr | |
| | | | 65 | | | | | 70 | | | | | 75 | |
| ggg | acg | tgt | acc | acc | atg | gga | gaa | cat | aga | aga | gaa aaa | aga tca gtg | 351 |
| Gly | Thr | Cys | Thr | Thr | Met | Gly | Glu | His | Arg | Arg | Glu Lys | Arg Ser Val | |
| | | 80 | | | | | 85 | | | | | 90 | | |
| gca | ctc | gtt | cca | cat | gtg | gga | atg | gga | ctg | gag | aca cga | act gaa aca | 399 |
| Ala | Leu | Val | Pro | His | Val | Gly | Met | Gly | Leu | Glu | Thr Arg | Thr Glu Thr | |
| | 95 | | | | | 100 | | | | | 105 | | | |
| tgg | atg | tca | tca | gaa | ggg | gcc | tgg | aaa | cat | gtc | cag aga | att gaa act | 447 |
| Trp | Met | Ser | Ser | Glu | Gly | Ala | Trp | Lys | His | Val | Gln Arg | Ile Glu Thr | |
| 110 | | | | | 115 | | | | | 120 | | | | 125 | |
| tgg | atc | ttg | aga | cat | cca | ggc | ttc | acc | atg | atg | gca gca | atc ctg gca | 495 |
| Trp | Ile | Leu | Arg | His | Pro | Gly | Phe | Thr | Met | Met | Ala Ala | Ile Leu Ala | |
| | | | | 130 | | | | | 135 | | | | 140 | |
| tac | acc | ata | gga | acg | aca | cat | ttc | caa | aga | gcc | ctg att | ttc atc tta | 543 |
| Tyr | Thr | Ile | Gly | Thr | Thr | His | Phe | Gln | Arg | Ala | Leu Ile | Phe Ile Leu | |
| | | | 145 | | | | | 150 | | | | | 155 | |
| ctg | aca | gct | gtc | act | cct | tca | atg | aca | atgcgttgca | taggaatgtc | | | 590 |
| Leu | Thr | Ala | Val | Thr | Pro | Ser | Met | Thr | | | | | |
| | 160 | | | | | 165 | | | | | | | | |

| | |

```
aaaagttgtg caaccagaaa acttggaata caccattgtg ataacacctc actcagggga    1010
agagcatgca gtcggaaatg acacaggaaa acatggcaag gaaatcaaaa taacaccaca    1070
gagttccatc acagaagcag aattgacagg ttatggcact gtcacaatgg agtgctctcc    1130
aagaacgggc ctcgacttca atgagatggt gttgttgcag atggaaaata aagcttggct    1190
ggtgcacagg caatggttcc tagacctgcc gttaccatgg ttgcccggag cggacacaca    1250
agggtcaaat tggatacaga aagagacatt ggtcactttc aaaaatcccc atgcgaagaa    1310
acaggatgtt gttgttttag gatcccaaga aggggccatg cacacagcac ttacaggggc    1370
cacagaaatc caaatgtcat caggaaactt actcttcaca ggacatctca agtgcaggct    1430
gagaatggac aagctacagc tcaaaggaat gtcatactct atgtgcacag gaaagtttaa    1490
agttgtggag cgaatagcag aaacacaaca tggaacaata gttatcagag tgcaatatga    1550
aggggacggc tctccatgca agatcccttt tgagataatg gatttggaaa aagacatgt    1610 cttaggtcgc ctgattacag tcaacccaat tgtgacagaa aaagatagcc gggtcaacat    1670
agaagcagaa cctccattcg gagacagcta catcatcata ggagtagagc cgggacaact    1730
gaagctcaac tggtttaaga aaggaagcac gctgggcaag gccttttcaa caactttgaa    1790
gggaggtaag tatcaaggtt acaagacagg tttaaggaga ccaatagaaa ctgggcttgt    1850
cgagacagag aagactcttg cgtttctgat aggcacctat ggtcttact gacatcccact    1910 ttgccttct ctccacagct caaagactgg cagcgttggg cgacacagcc tgggactttg    1970
gctctattgg aggggtcttc aactccatag gaaaagccgt tcaccaagtg tttggtggtg    2030
ccttcagaac actctttggg ggaatgtctt ggatcacaca agggctaatg ggtgccctac    2090
tgctctggat gggcgtcaac gcacgagacc gatcaattgc tttggccttc ttagccacag    2150
ggggtgtgct cgtgttctta gcgaccaatg tgcatgctta a                        2191
```

<210> SEQ ID NO 8
<211> LENGTH: 166
<212> TYPE: PRT
<213> ORGANISM: Artificial Sequence
<220> FEATURE:
<223> OTHER INFORMATION: Synthetic Construct

<400> SEQUENCE: 8

Phe His Leu Thr Thr Arg Asn Gly Glu Pro His Met Ile Val Ser Arg
1               5                   10                  15

Gln Glu Lys Gly Lys Ser Leu Leu Phe Lys Thr Glu Asp Gly Val Asn
            20                  25                  30

Met Cys Thr Leu Met Ala Met Asp Leu Gly Glu Leu Cys Glu Asp Thr
        35                  40                  45

Ile Thr Tyr Lys Cys Pro Leu Leu Arg Gln Asn Glu Pro Glu Asp Ile
    50                  55                  60

Asp Cys Trp Cys Asn Ser Thr Ser Thr Trp Val Thr Tyr Gly Thr Cys
65                  70                  75                  80

Thr Thr Met Gly Glu His Arg Arg Glu Lys Arg Ser Val Ala Leu Val
                85                  90                  95

Pro His Val Gly Met Gly Leu Glu Thr Arg Thr Glu Thr Trp Met Ser
            100                 105                 110

Ser Glu Gly Ala Trp Lys His Val Gln Arg Ile Glu Thr Trp Ile Leu
        115                 120                 125

Arg His Pro Gly Phe Thr Met Met Ala Ala Ile Leu Ala Tyr Thr Ile
    130                 135                 140

```
Gly Thr Thr His Phe Gln Arg Ala Leu Ile Phe Ile Leu Leu Thr Ala
145                 150                 155                 160

Val Thr Pro Ser Met Thr
                165
```

<210> SEQ ID NO 9
<211> LENGTH: 495
<212> TYPE: PRT
<213> ORGANISM: Artificial Sequence
<220> FEATURE:
<223> OTHER INFORMATION: DENV2 RDERR E protein

<400> SEQUENCE: 9

```
Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
            35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Arg Asp Phe Gly Lys Gly Gly
            100                 105                 110

Ile Val Thr Cys Ala Met Phe Arg Cys Lys Lys Asn Met Glu Gly Lys
        115                 120                 125

Val Val Gln Pro Glu Asn Leu Glu Tyr Thr Ile Val Ile Thr Pro His
    130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Glu Arg Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335
```

```
Phe Glu Ile Met Asp Leu Glu Lys Arg His Val Leu Gly Arg Leu Ile
                340                 345                 350
Thr Val Asn Pro Ile Val Thr Glu Lys Asp Ser Arg Val Asn Ile Glu
            355                 360                 365
Ala Glu Pro Pro Phe Gly Asp Ser Tyr Ile Ile Gly Val Glu Pro
370                 375                 380
Gly Gln Leu Lys Leu Asn Trp Phe Lys Lys Gly Ser Thr Leu Gly Lys
385                 390                 395                 400
Ala Phe Ser Thr Thr Leu Lys Gly Ala Gln Arg Leu Ala Ala Leu Gly
                405                 410                 415
Asp Thr Ala Trp Asp Phe Gly Ser Ile Gly Gly Val Phe Asn Ser Ile
                420                 425                 430
Gly Lys Ala Val His Gln Val Phe Gly Gly Ala Phe Arg Thr Leu Phe
                435                 440                 445
Gly Gly Met Ser Trp Ile Thr Gln Gly Leu Met Gly Ala Leu Leu Leu
                450                 455                 460
Trp Met Gly Val Asn Ala Arg Asp Arg Ser Ile Ala Leu Ala Phe Leu
465                 470                 475                 480
Ala Thr Gly Gly Val Leu Val Phe Leu Ala Thr Asn Val His Ala
                485                 490                 495

<210> SEQ ID NO 10
<211> LENGTH: 2191
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (73)..(570)
<223> OTHER INFORMATION: prM coding sequence
<220> FEATURE:
<221> NAME/KEY: misc_feature
<222> LOCATION: (571)..(1795)
<223> OTHER INFORMATION: E coding sequence
<220> FEATURE:
<221> NAME/KEY: misc_feature
<222> LOCATION: (1796)..(1928)
<223> OTHER INFORMATION: intron
<220> FEATURE:
<221> NAME/KEY: misc_feature
<222> LOCATION: (1929)..(2188)
<223> OTHER INFORMATION: E coding sequence

<400> SEQUENCE: 10
atgggcaaga ggtccgccgg ctcaatcatg tggctcgcga gcttggcagt tgtcatagct    60
tgtgcaggcg cc ttc cat tta acc aca cgt aac gga gaa cca cac atg atc   111
           Phe His Leu Thr Thr Arg Asn Gly Glu Pro His Met Ile
             1               5                  10 gtc agc aga caa gag aaa ggg aaa agt ctt ctg ttt aaa aca gag gat    159
Val Ser Arg Gln Glu Lys Gly Lys Ser Leu Leu Phe Lys Thr Glu Asp
 15                  20                  25 ggc gtg aac atg tgt acc ctc atg gcc atg gac ctt ggt gaa ttg tgt    207
Gly Val Asn Met Cys Thr Leu Met Ala Met Asp Leu Gly Glu Leu Cys
 30                  35                  40                  45 gaa gac aca atc acg tac aag tgt ccc ctt ctc agg cag aat gag cca    255
Glu Asp Thr Ile Thr Tyr Lys Cys Pro Leu Leu Arg Gln Asn Glu Pro
                50                  55                  60 gaa gac ata gac tgt tgg tgc aac tct acg tcc acg tgg gta act tat    303
Glu Asp Ile Asp Cys Trp Cys Asn Ser Thr Ser Thr Trp Val Thr Tyr
             65                  70                  75
```

```
ggg acg tgt acc acc atg gga gaa cat aga aga gaa aaa aga tca gtg        351
Gly Thr Cys Thr Thr Met Gly Glu His Arg Arg Glu Lys Arg Ser Val
         80                  85                  90 gca ctc gtt cca cat gtg gga atg gga ctg gag aca cga act gaa aca        399
Ala Leu Val Pro His Val Gly Met Gly Leu Glu Thr Arg Thr Glu Thr
 95                 100                 105 tgg atg tca tca gaa ggg gcc tgg aaa cat gtc cag aga att gaa act        447
Trp Met Ser Ser Glu Gly Ala Trp Lys His Val Gln Arg Ile Glu Thr
110                 115                 120                 125 tgg atc ttg aga cat cca ggc ttc acc atg atg gca gca atc ctg gca        495
Trp Ile Leu Arg His Pro Gly Phe Thr Met Met Ala Ala Ile Leu Ala
                130                 135                 140 tac acc ata gga acg aca cat ttc caa aga gcc ctg att ttc atc tta        543
Tyr Thr Ile Gly Thr Thr His Phe Gln Arg Ala Leu Ile Phe Ile Leu
            145                 150                 155 ctg aca gct gtc act cct tca atg aca atgcgttgca taggaatgtc              590
Leu Thr Ala Val Thr Pro Ser Met Thr
            160                 165 aaatagagac tttgtggaag gggtttcagg aggaagctgg gttgacatag tcttagaaca       650
tgggagctgt gtgacgacga tggcaaaaaa caaaccaaca ttggattttg aactgataaa       710
aacagaagcc aaacagcctg ccaccctaag gaagtactgt atagaggcaa agctaaccaa       770
cacaacaaca gaatctcgct gcccaacaca aggggaaccc agcctaaatg aagagcagga       830
caaaaggttc gtctgcaaac actccatggt agacagagga tggggaaatg gatgtcgcga       890
ctttggaaag ggaggcattg tgacctgtgc tatgttcaga tgcaaaaaga acatggaagg       950
aaaagttgtg caaccagaaa acttggaata caccattgtg ataacacctc actcaggga      1010 agagcatgca gtcggaaatg acacaggaaa acatggcaag gaaatcaaaa taacaccaca      1070
gagttccatc acagaagcag aattgacagg ttatggcact gtcacaatgg agtgctctcc      1130
aagaacgggc ctcgacttca atgagatggt gttgttgcag atggaaaata agcttggct       1190 ggtgcacagg caatggttcc tagacctgcc gttaccatgg ttgcccggag cggacacaca      1250
agggtcaaat tggatacaga aagagacatt ggtcactttc aaaaatcccc atgcgaagaa      1310
acaggatgtt gttgttttag atcccaaga agggggccatg cacacagcac ttacaggggc      1370
cacagaaatc caaatgtcat caggaaactt actcttcaca ggacatctca gtgcaggct      1430 gagaatggac aagctacagc tcaaaggaat gtcatactct atgtgcacag gaaagtttaa      1490
agttgtggag cgaatagcag aaacacaaca tggaacaata gttatcagag tgcaatatga      1550
aggggacggc tctccatgca agatccctt tgagataatg gatttggaaa aagacatgt       1610 cttaggtcgc ctgattacag tcaacccaat tgtgacagaa aagatagcc gggtcaacat      1670 agaagcagaa cctccattcg agacagcta catcatcata ggagtagagc cgggacaact      1730
gaagctcaac tggtttaaga aggaagcac gctgggcaag gccttttcaa caactttgaa      1790
gggaggtaag tatcaaggtt acaagacagg tttaaggaga ccaatagaaa ctgggcttgt      1850
cgagacagag aagactcttg cgtttctgat aggcacctat ggtcttact gacatccact      1910 ttgccttttct ctccacagct caaagactgg cagcgttggg cgacacagcc tgggactttg     1970
gctctattgg aggggtcttc aactccatag gaaaagccgt tcaccaagtg tttggtggtg      2030
ccttcagaac actctttggg ggaatgtctt ggatcacaca agggctaatg ggtgccctac      2090
tgctctggat gggcataaac gcacgagacc gatcaattgc tttgaccttc ttagccgtag      2150
ggggtgtgct cctgttctta gcgaccaatg tgcatgctta a                          2191
```

```
<210> SEQ ID NO 11
<211> LENGTH: 166
<212> TYPE: PRT
<213> ORGANISM: Artificial Sequence
<220> FEATURE:
<223> OTHER INFORMATION: Synthetic Construct

<400> SEQUENCE: 11

Phe His Leu Thr Thr Arg Asn Gly Glu Pro His Met Ile Val Ser Arg
1               5                   10                  15

Gln Glu Lys Gly Lys Ser Leu Leu Phe Lys Thr Glu Asp Gly Val Asn
                20                  25                  30

Met Cys Thr Leu Met Ala Met Asp Leu Gly Glu Leu Cys Glu Asp Thr
            35                  40                  45

Ile Thr Tyr Lys Cys Pro Leu Leu Arg Gln Asn Glu Pro Glu Asp Ile
    50                  55                  60

Asp Cys Trp Cys Asn Ser Thr Ser Thr Trp Val Thr Tyr Gly Thr Cys
65                  70                  75                  80

Thr Thr Met Gly Glu His Arg Arg Glu Lys Arg Ser Val Ala Leu Val
                85                  90                  95

Pro His Val Gly Met Gly Leu Glu Thr Arg Thr Glu Thr Trp Met Ser
            100                 105                 110

Ser Glu Gly Ala Trp Lys His Val Gln Arg Ile Glu Thr Trp Ile Leu
        115                 120                 125

Arg His Pro Gly Phe Thr Met Met Ala Ala Ile Leu Ala Tyr Thr Ile
    130                 135                 140

Gly Thr Thr His Phe Gln Arg Ala Leu Ile Phe Ile Leu Leu Thr Ala
145                 150                 155                 160

Val Thr Pro Ser Met Thr
                165

<210> SEQ ID NO 12
<211> LENGTH: 495
<212> TYPE: PRT
<213> ORGANISM: Artificial Sequence
<220> FEATURE:
<223> OTHER INFORMATION: DENV2 RDERR-TMD E protein

<400> SEQUENCE: 12

Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
                20                  25                  30

Thr Met Ala Lys Asn Lys Pro Thr Leu Asp Phe Glu Leu Ile Lys Thr
            35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Arg Asp Phe Lys Gly Gly
            100                 105                 110

Ile Val Thr Cys Ala Met Phe Arg Cys Lys Lys Asn Met Glu Gly Lys
        115                 120                 125

Val Val Gln Pro Glu Asn Leu Glu Tyr Thr Ile Val Ile Thr Pro His
    130                 135                 140
```

```
Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
            165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
            245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Glu Arg Ile Ala Glu Thr Gln His Gly Thr Ile
305                 310                 315                 320

Val Ile Arg Val Gln Tyr Glu Gly Asp Gly Ser Pro Cys Lys Ile Pro
            325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Arg Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asn Trp Phe Lys Lys Gly Ser Thr Leu Gly Lys
385                 390                 395                 400

Ala Phe Ser Thr Thr Leu Lys Gly Ala Gln Arg Leu Ala Ala Leu Gly
            405                 410                 415

Asp Thr Ala Trp Asp Phe Gly Ser Ile Gly Gly Val Phe Asn Ser Ile
            420                 425                 430

Gly Lys Ala Val His Gln Val Phe Gly Gly Ala Phe Arg Thr Leu Phe
        435                 440                 445

Gly Gly Met Ser Trp Ile Thr Gln Gly Leu Met Gly Ala Leu Leu Leu
    450                 455                 460

Trp Met Gly Ile Asn Ala Arg Asp Arg Ser Ile Ala Leu Thr Phe Leu
465                 470                 475                 480

Ala Val Gly Gly Val Leu Leu Phe Leu Ala Thr Asn Val His Ala
            485                 490                 495

<210> SEQ ID NO 13
<211> LENGTH: 81
<212> TYPE: PRT
<213> ORGANISM: Dengue virus type 2

<400> SEQUENCE: 13

Leu Gly Asp Thr Ala Trp Asp Phe Gly Ser Leu Gly Gly Val Phe Thr
1               5                   10                  15

Ser Ile Gly Lys Ala Leu His Gln Val Phe Gly Ala Ile Tyr Gly Ala
            20                  25                  30
```

```
Ala Phe Ser Gly Val Ser Trp Thr Met Lys Ile Leu Ile Gly Val Ile
            35                  40                  45

Ile Thr Trp Ile Gly Met Asn Ser Arg Ser Thr Ser Leu Ser Val Ser
 50                  55                  60

Leu Val Leu Val Gly Val Val Thr Leu Tyr Leu Gly Ala Met Val Gln
 65                  70                  75                  80

Ala
```

```
<210> SEQ ID NO 14
<211> LENGTH: 81
<212> TYPE: PRT
<213> ORGANISM: Dengue virus type 1

<400> SEQUENCE: 14

Leu Gly Asp Thr Ala Trp Asp Phe Gly Ser Ile Gly Gly Val Phe Thr
 1               5                  10                  15

Ser Val Gly Lys Leu Ile His Gln Ile Phe Gly Thr Ala Tyr Gly Val
            20                  25                  30

Leu Phe Ser Gly Val Ser Trp Thr Met Lys Ile Gly Ile Gly Ile Leu
            35                  40                  45

Leu Thr Trp Leu Gly Leu Asn Ser Arg Ser Thr Ser Leu Ser Met Thr
 50                  55                  60

Cys Ile Ala Val Gly Met Val Thr Leu Tyr Leu Gly Val Met Val Gln
 65                  70                  75                  80

Ala
```

```
<210> SEQ ID NO 15
<211> LENGTH: 81
<212> TYPE: PRT
<213> ORGANISM: Dengue virus type 3

<400> SEQUENCE: 15

Leu Gly Asp Thr Ala Trp Asp Phe Gly Ser Val Gly Gly Val Leu Asn
 1               5                  10                  15

Ser Leu Gly Lys Met Val His Gln Ile Phe Gly Ser Ala Tyr Thr Ala
            20                  25                  30

Leu Phe Ser Gly Val Ser Trp Ile Met Lys Ile Gly Ile Gly Val Leu
            35                  40                  45

Leu Thr Trp Ile Gly Leu Asn Ser Lys Asn Thr Ser Met Ser Phe Ser
 50                  55                  60

Cys Ile Ala Ile Gly Ile Ile Thr Leu Tyr Leu Gly Val Val Val Gln
 65                  70                  75                  80

Ala
```

```
<210> SEQ ID NO 16
<211> LENGTH: 81
<212> TYPE: PRT
<213> ORGANISM: Dengue virus type 4

<400> SEQUENCE: 16

Leu Gly Glu Thr Ala Trp Asp Phe Gly Ser Val Gly Gly Leu Phe Thr
 1               5                  10                  15

Ser Leu Gly Lys Ala Val His Gln Val Phe Gly Ser Val Tyr Thr Thr
            20                  25                  30

Met Phe Gly Gly Val Ser Trp Met Ile Arg Ile Leu Ile Gly Phe Leu
            35                  40                  45
```

-continued

Val Leu Trp Ile Gly Thr Asn Ser Arg Asn Thr Ser Met Ala Met Thr
            50                  55                  60

Cys Ile Ala Val Gly Gly Ile Thr Leu Phe Leu Gly Phe Thr Val Gln
 65                  70                  75                  80

Ala

<210> SEQ ID NO 17
<211> LENGTH: 81
<212> TYPE: PRT
<213> ORGANISM: West Nile virus

<400> SEQUENCE: 17

Leu Gly Asp Thr Ala Trp Asp Phe Gly Ser Val Gly Gly Val Phe Thr
 1               5                  10                  15

Ser Val Gly Lys Ala Val His Gln Val Phe Gly Gly Ala Phe Arg Ser
                20                  25                  30

Leu Phe Gly Gly Met Ser Trp Ile Thr Gln Gly Leu Leu Gly Ala Leu
         35                  40                  45

Leu Leu Trp Met Gly Ile Asn Ala Arg Asp Arg Ser Ile Ala Leu Thr
     50                  55                  60

Phe Leu Ala Val Gly Gly Val Leu Leu Phe Leu Ser Val Asn Val His
 65                  70                  75                  80

Ala

<210> SEQ ID NO 18
<211> LENGTH: 81
<212> TYPE: PRT
<213> ORGANISM: Japanese encephalitis virus

<400> SEQUENCE: 18

Leu Gly Asp Thr Ala Trp Asp Phe Gly Ser Ile Gly Gly Val Phe Asn
 1               5                  10                  15

Ser Ile Gly Lys Ala Val His Gln Val Phe Gly Gly Ala Phe Arg Thr
                20                  25                  30

Leu Phe Gly Gly Met Ser Trp Ile Thr Gln Gly Leu Met Gly Ala Leu
         35                  40                  45

Leu Leu Trp Met Gly Val Asn Ala Arg Asp Arg Ser Ile Ala Leu Ala
     50                  55                  60

Phe Leu Ala Thr Gly Gly Val Leu Val Phe Leu Ala Thr Asn Val His
 65                  70                  75                  80

Ala

<210> SEQ ID NO 19
<211> LENGTH: 81
<212> TYPE: PRT
<213> ORGANISM: Murray Valley encephalitis virus

<400> SEQUENCE: 19

Leu Gly Asp Thr Ala Trp Asp Phe Gly Ser Val Gly Gly Val Phe Asn
 1               5                  10                  15

Ser Ile Gly Lys Ala Val His Gln Val Phe Gly Gly Ala Phe Arg Thr
                20                  25                  30

Leu Phe Gly Gly Met Ser Trp Ile Ser Pro Gly Leu Leu Gly Ala Leu
         35                  40                  45

Leu Leu Trp Met Gly Val Asn Ala Arg Asp Lys Ser Ile Ala Leu Ala
     50                  55                  60

Phe Leu Ala Thr Gly Gly Val Leu Leu Phe Leu Ala Thr Asn Val His

```
                        65                  70                  75                  80

Ala

<210> SEQ ID NO 20
<211> LENGTH: 81
<212> TYPE: PRT
<213> ORGANISM: St. Louis encephalitis virus

<400> SEQUENCE: 20

Leu Gly Asp Thr Ala Trp Asp Phe Gly Ser Ile Gly Gly Val Phe Asn
1               5                   10                  15

Ser Ile Gly Lys Ala Val His Gln Val Phe Gly Gly Ala Phe Arg Thr
            20                  25                  30

Leu Phe Gly Gly Met Ser Trp Ile Thr Gln Gly Leu Leu Gly Ala Leu
        35                  40                  45

Leu Leu Trp Met Gly Leu Gln Ala Arg Asp Arg Ser Ile Ser Leu Thr
    50                  55                  60

Leu Leu Ala Thr Gly Gly Ile Leu Ile Phe Leu Ala Thr Ser Val Gln
65                  70                  75                  80

Ala

<210> SEQ ID NO 21
<211> LENGTH: 81
<212> TYPE: PRT
<213> ORGANISM: Yellow fever virus

<400> SEQUENCE: 21

Met Gly Asp Ala Ala Trp Asp Phe Ser Ser Ala Gly Gly Phe Phe Thr
1               5                   10                  15

Ser Val Gly Lys Gly Ile His Thr Val Phe Gly Ser Ala Phe Gln Gly
            20                  25                  30

Leu Phe Gly Gly Leu Asn Trp Ile Thr Lys Val Ile Met Gly Ala Val
        35                  40                  45

Leu Ile Trp Val Gly Ile Asn Thr Arg Asn Met Thr Met Ser Met Ser
    50                  55                  60

Met Ile Leu Val Gly Val Ile Met Met Phe Leu Ser Leu Gly Val Gly
65                  70                  75                  80

Ala

<210> SEQ ID NO 22
<211> LENGTH: 81
<212> TYPE: PRT
<213> ORGANISM: Tick-borne encephalitis virus

<400> SEQUENCE: 22

Ile Gly Glu His Ala Trp Asp Phe Gly Ser Ala Gly Gly Phe Leu Ser
1               5                   10                  15

Ser Ile Gly Lys Ala Val His Thr Val Leu Gly Gly Ala Phe Asn Ser
            20                  25                  30

Ile Phe Gly Gly Val Gly Phe Leu Pro Lys Leu Leu Leu Gly Val Ala
        35                  40                  45

Leu Ala Trp Leu Gly Leu Asn Met Arg Asn Pro Thr Met Ser Met Ser
    50                  55                  60

Phe Leu Leu Ala Gly Gly Leu Val Leu Ala Met Thr Leu Gly Val Gly
65                  70                  75                  80

Ala
```

<210> SEQ ID NO 23
<211> LENGTH: 81
<212> TYPE: PRT
<213> ORGANISM: Artificial Sequence
<220> FEATURE:
<223> OTHER INFORMATION: Synthetic polypeptide

<400> SEQUENCE: 23

```
Leu Gly Asp Thr Ala Trp Asp Phe Gly Ser Leu Gly Val Phe Thr
1               5                   10                  15

Ser Ile Gly Lys Ala Leu His Gln Val Phe Gly Ala Ile Tyr Gly Ala
            20                  25                  30

Ala Phe Ser Gly Val Ser Trp Thr Met Lys Ile Leu Ile Gly Val Ile
        35                  40                  45

Ile Thr Trp Ile Gly Ile Asn Ser Arg Ser Thr Ser Leu Ser Val Thr
    50                  55                  60

Leu Val Leu Val Gly Val Val Thr Leu Tyr Leu Gly Ala Met Val Gln
65                  70                  75                  80

Ala
```

<210> SEQ ID NO 24
<211> LENGTH: 81
<212> TYPE: PRT
<213> ORGANISM: Artificial Sequence
<220> FEATURE:
<223> OTHER INFORMATION: Synthetic polypeptide

<400> SEQUENCE: 24

```
Leu Gly Asp Thr Ala Trp Asp Phe Gly Ser Ile Gly Gly Val Phe Thr
1               5                   10                  15

Ser Val Gly Lys Leu Ile His Gln Ile Phe Gly Thr Ala Tyr Gly Val
            20                  25                  30

Leu Phe Ser Gly Val Ser Trp Thr Met Lys Ile Gly Ile Gly Ile Leu
        35                  40                  45

Leu Thr Trp Leu Gly Ile Asn Ser Arg Ser Thr Ser Leu Ser Met Thr
    50                  55                  60

Cys Ile Ala Val Gly Met Val Thr Leu Tyr Leu Gly Val Met Val Gln
65                  70                  75                  80

Ala
```

<210> SEQ ID NO 25
<211> LENGTH: 81
<212> TYPE: PRT
<213> ORGANISM: Artificial Sequence
<220> FEATURE:
<223> OTHER INFORMATION: Synthetic polypeptide

<400> SEQUENCE: 25

```
Leu Gly Asp Thr Ala Trp Asp Phe Gly Ser Val Gly Gly Val Leu Asn
1               5                   10                  15

Ser Leu Gly Lys Met Val His Gln Ile Phe Gly Ser Ala Tyr Thr Ala
            20                  25                  30

Leu Phe Ser Gly Val Ser Trp Ile Met Lys Ile Gly Ile Gly Val Leu
        35                  40                  45

Leu Thr Trp Ile Gly Ile Asn Ser Lys Asn Thr Ser Met Ser Phe Thr
    50                  55                  60

Cys Ile Ala Val Gly Ile Ile Thr Leu Tyr Leu Gly Val Val Val Gln
65                  70                  75                  80
```

<210> SEQ ID NO 26
<211> LENGTH: 81
<212> TYPE: PRT
<213> ORGANISM: Artificial Sequence
<220> FEATURE:
<223> OTHER INFORMATION: Synthetic polypeptide

<400> SEQUENCE: 26

```
Leu Gly Glu Thr Ala Trp Asp Phe Gly Ser Val Gly Leu Phe Thr
1               5                   10                  15

Ser Leu Gly Lys Ala Val His Gln Val Phe Gly Ser Val Tyr Thr Thr
                20                  25                  30

Met Phe Gly Gly Val Ser Trp Met Ile Arg Ile Leu Ile Gly Phe Leu
            35                  40                  45

Val Leu Trp Ile Gly Ile Asn Ser Arg Asn Thr Ser Met Ala Met Thr
        50                  55                  60

Cys Ile Ala Val Gly Gly Ile Thr Leu Phe Leu Gly Phe Thr Val Gln
65                  70                  75                  80

Ala
```

<210> SEQ ID NO 27
<211> LENGTH: 81
<212> TYPE: PRT
<213> ORGANISM: Artificial Sequence
<220> FEATURE:
<223> OTHER INFORMATION: Synthetic polypeptide

<400> SEQUENCE: 27

```
Leu Gly Asp Thr Ala Trp Asp Phe Gly Ser Ile Gly Gly Val Phe Asn
1               5                   10                  15

Ser Ile Gly Lys Ala Val His Gln Val Phe Gly Gly Ala Phe Arg Thr
                20                  25                  30

Leu Phe Gly Gly Met Ser Trp Ile Thr Gln Gly Leu Met Gly Ala Leu
            35                  40                  45

Leu Leu Trp Met Gly Ile Asn Ala Arg Asp Arg Ser Ile Ala Leu Thr
        50                  55                  60

Phe Leu Ala Val Gly Gly Val Leu Leu Phe Leu Ala Thr Asn Val His
65                  70                  75                  80

Ala
```

<210> SEQ ID NO 28
<211> LENGTH: 81
<212> TYPE: PRT
<213> ORGANISM: Artificial Sequence
<220> FEATURE:
<223> OTHER INFORMATION: Synthetic polypeptide

<400> SEQUENCE: 28

```
Leu Gly Asp Thr Ala Trp Asp Phe Gly Ser Val Gly Gly Val Phe Asn
1               5                   10                  15

Ser Ile Gly Lys Ala Val His Gln Val Phe Gly Gly Ala Phe Arg Thr
                20                  25                  30

Leu Phe Gly Gly Met Ser Trp Ile Ser Pro Gly Leu Leu Gly Ala Leu
            35                  40                  45

Leu Leu Trp Met Gly Ile Asn Ala Arg Asp Lys Ser Ile Ala Leu Thr
        50                  55                  60

Phe Leu Ala Val Gly Gly Val Leu Leu Phe Leu Ala Thr Asn Val His
```

```
                  65                  70                  75                  80
Ala

<210> SEQ ID NO 29
<211> LENGTH: 81
<212> TYPE: PRT
<213> ORGANISM: Artificial Sequence
<220> FEATURE:
<223> OTHER INFORMATION: Synthetic polypeptide

<400> SEQUENCE: 29

Leu Gly Asp Thr Ala Trp Asp Phe Gly Ser Ile Gly Gly Val Phe Asn
1               5                   10                  15

Ser Ile Gly Lys Ala Val His Gln Val Phe Gly Gly Ala Phe Arg Thr
            20                  25                  30

Leu Phe Gly Gly Met Ser Trp Ile Thr Gln Gly Leu Leu Gly Ala Leu
        35                  40                  45

Leu Leu Trp Met Gly Ile Gln Ala Arg Asp Arg Ser Ile Ser Leu Thr
    50                  55                  60

Leu Leu Ala Val Gly Gly Ile Leu Leu Phe Leu Ala Thr Ser Val Gln
65                  70                  75                  80

Ala

<210> SEQ ID NO 30
<211> LENGTH: 81
<212> TYPE: PRT
<213> ORGANISM: Artificial Sequence
<220> FEATURE:
<223> OTHER INFORMATION: Synthetic polypeptide

<400> SEQUENCE: 30

Met Gly Asp Ala Ala Trp Asp Phe Ser Ser Ala Gly Gly Phe Phe Thr
1               5                   10                  15

Ser Val Gly Lys Gly Ile His Thr Val Phe Gly Ser Ala Phe Gln Gly
            20                  25                  30

Leu Phe Gly Gly Leu Asn Trp Ile Thr Lys Val Ile Met Gly Ala Val
        35                  40                  45

Leu Ile Trp Val Gly Ile Asn Thr Arg Asn Met Thr Met Ser Met Thr
    50                  55                  60

Met Ile Leu Val Gly Val Ile Met Leu Phe Leu Ser Leu Gly Val Gly
65                  70                  75                  80

Ala

<210> SEQ ID NO 31
<211> LENGTH: 81
<212> TYPE: PRT
<213> ORGANISM: Artificial Sequence
<220> FEATURE:
<223> OTHER INFORMATION: Synthetic polypeptide

<400> SEQUENCE: 31

Ile Gly Glu His Ala Trp Asp Phe Gly Ser Ala Gly Gly Phe Leu Ser
1               5                   10                  15

Ser Ile Gly Lys Ala Val His Thr Val Leu Gly Gly Ala Phe Asn Ser
            20                  25                  30

Ile Phe Gly Gly Val Gly Phe Leu Pro Lys Leu Leu Leu Gly Val Ala
        35                  40                  45

Leu Ala Trp Leu Gly Ile Asn Met Arg Asn Pro Thr Met Ser Met Thr
    50                  55                  60
```

Phe Leu Leu Val Gly Gly Leu Val Leu Ala Met Thr Leu Gly Val Gly
65                  70                  75                  80

Ala

<210> SEQ ID NO 32
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 32

Thr Gln Gly Leu Leu Gly Ala Leu Leu Leu Trp Met Gly Ile Asn
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 33

Gln Gly Leu Met Gly Ala Leu Leu Leu Trp Met Gly Val Asn Ala
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 34

Gly Ala Leu Leu Leu Trp Met Gly Ile Asn Ala Arg Asp Arg Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 35

Ala Leu Leu Leu Trp Met Gly Val Asn Ala Arg Asp Arg Ser Ile
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 36

Trp Met Gly Ile Asn Ala Arg Asp Arg Ser Ile Ala Leu Thr Phe
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic polypeptide -continued

```
<400> SEQUENCE: 37

Met Gly Val Asn Ala Arg Asp Arg Ser Ile Ala Leu Ala Phe Leu
1               5                   10                  15

<210> SEQ ID NO 38
<211> LENGTH: 501
<212> TYPE: PRT
<213> ORGANISM: West Nile virus

<400> SEQUENCE: 38

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Glu Val Arg Ser Tyr Cys Tyr Leu Ala Thr
    50                  55                  60

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
    130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205

Lys Thr Phe Leu Val His Arg Glu Trp Phe Met Asp Leu Asn Leu Pro
    210                 215                 220

Trp Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
                245                 250                 255

Ser Gln Glu Gly Ala Leu His Gln Ala Leu Ala Gly Ala Ile Pro Val
            260                 265                 270

Glu Phe Ser Ser Asn Thr Val Lys Leu Thr Ser Gly His Leu Lys Cys
        275                 280                 285

Arg Val Lys Met Glu Lys Leu Gln Leu Lys Gly Thr Thr Tyr Gly Val
    290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
                325                 330                 335

Lys Val Pro Ile Ser Ser Val Ala Ser Leu Asn Asp Leu Thr Pro Val
            340                 345                 350
```

```
Gly Arg Leu Val Thr Val Asn Pro Phe Val Ser Val Ala Thr Ala Asn
        355                 360                 365

Ala Lys Val Leu Ile Glu Leu Glu Pro Pro Phe Gly Asp Ser Tyr Ile
    370                 375                 380

Val Val Gly Arg Gly Glu Gln Gln Ile Asn His His Trp His Lys Ser
385                 390                 395                 400

Gly Ser Ser Ile Gly Lys Ala Phe Thr Thr Thr Leu Lys Gly Ala Gln
                405                 410                 415

Arg Leu Ala Ala Leu Gly Asp Thr Ala Trp Asp Phe Gly Ser Val Gly
            420                 425                 430

Gly Val Phe Thr Ser Val Gly Lys Ala Val His Gln Val Phe Gly Gly
        435                 440                 445

Ala Phe Arg Ser Leu Phe Gly Gly Met Ser Trp Ile Thr Gln Gly Leu
    450                 455                 460

Leu Gly Ala Leu Leu Leu Trp Met Gly Ile Asn Ala Arg Asp Arg Ser
465                 470                 475                 480

Ile Ala Leu Thr Phe Leu Ala Val Gly Gly Val Leu Leu Phe Leu Ser
            485                 490                 495

Val Asn Val His Ala
            500
```